United States Patent
Han et al.

(10) Patent No.: US 7,129,378 B2
(45) Date of Patent: Oct. 31, 2006

(54) METHOD OF PREPARING AMINE STEREOISOMERS

(75) Inventors: Zhengxu Han, Shrewesbury, MA (US);
Dhileepkumar Krishnamurthy, Danbury, CT (US); Chris Hugh Senanayake, Brookfield, CT (US); Zhi-Hui Lu, Shrewsbury, MA (US)

(73) Assignee: Apsinterm, LLC, Wilmington, DE (US)

( * ) Notice: Subject to any disclaimer, the term of this patent is extended or adjusted under 35 U.S.C. 154(b) by 0 days.

(21) Appl. No.: 10/508,941

(22) PCT Filed: Apr. 7, 2003

(86) PCT No.: PCT/US03/08827

§ 371 (c)(1),
(2), (4) Date: Mar. 2, 2005

(87) PCT Pub. No.: WO03/091207

PCT Pub. Date: Nov. 6, 2003

(65) Prior Publication Data

US 2005/0165240 A1 Jul. 28, 2005

Related U.S. Application Data

(60) Provisional application No. 60/371,158, filed on Apr. 10, 2002.

(51) Int. Cl.
*C07C 209/62* (2006.01)
(52) U.S. Cl. .................. 564/248; 564/338; 564/415

(58) Field of Classification Search ................ 564/248, 564/338, 415
See application file for complete search history.

(56) References Cited

U.S. PATENT DOCUMENTS

| 4,562,185 A | 12/1985 | Jager et al. | |
|---|---|---|---|
| 4,746,680 A * | 5/1988 | Jeffery et al. | ............... 514/646 |
| 5,271,812 A | 12/1993 | Gao et al. | |
| 6,610,887 B1 | 8/2003 | Senanayake et al. | |

FOREIGN PATENT DOCUMENTS

| WO | WO02/083608 | 10/2002 |
|---|---|---|
| WO | WO02/083631 | 10/2002 |

OTHER PUBLICATIONS

Liu et al., J. Am. Chem. Soc., 1997, 119, 9913-9914.

* cited by examiner

*Primary Examiner*—Samuel Barts
(74) *Attorney, Agent, or Firm*—Martin A. Hay

(57) ABSTRACT

This invention provides a method of preparing amine stereoisomers, which comprises stereoselectively reducing a sulfinylimine that bears on the sulfinyl group a residue of an alcohol, thiol or amine, or reacting a sulfinylimine stereoisomer that bears on the sulfinyl group a residue of an alcohol, thiol or amine with a source of a nucleophile, to afford a sulfinylamine stereoisomer, followed by contacting the sulfinylamine stereoisomer with a reagent suitable for the cleavage of a sulfur-nitrogen bond, to afford an amine stereoisomer. It also provides novel intermediates useful in the method, and the use of certain of the intermediates in the preparation of sulfoxide and sulfinylamine stereoisomers.

32 Claims, No Drawings

METHOD OF PREPARING AMINE STEREOISOMERS

This application claims the benefit of U.S. provisional patent application Ser. No. 60/371,158, filed 10 Apr. 2002.

This invention relates to a method of preparing amine stereoisomers, to novel intermediates useful in the method and to use of certain of the novel intermediates in a method of preparing sulfoxide and sulfinylamine stereoisomers.

Many amine stereoisomers possess useful biological properties. For example, sibutramine is a neuronal monoamine reuptake inhibitor, which has the chemical name [N-1-[1-(4-chlorophenyl)cyclobutyl]-3-methylbutyl]-N,N-dimethylamine. Originally disclosed in U.S. Pat. Nos. 4,746,680 and 4,806,570, sibutramine inhibits the reuptake of norepinephrine and, to a lesser extent, serotonin and dopamine. See, e.g., Buckett et al., *Prog. Neuro-psychopharn. & Biol. Psychiat.*, 12:575–584, 1988; King et al., *J. Clin. Pharm.*, 26:607–611 (1989).

Racemic sibutramine is sold as a hydrochloride monohydrate under the tradename MERIDIA®, and is indicated for the treatment of obesity. *Physician's Desk Reference*®1509–1513 (54$^{th}$ ed., 2000). The treatment of obesity using racemic sibutramine is disclosed, for example, in U.S. Pat. No. 5,436,272.

Sibutramine is rapidly absorbed from the gastrointestinal tract following oral administration and undergoes an extensive first-pass metabolism that yields the metabolites desmethylsibutramine ("DMS") and didesmethylsibutramine ("DDMS"), as shown below in Scheme 1.

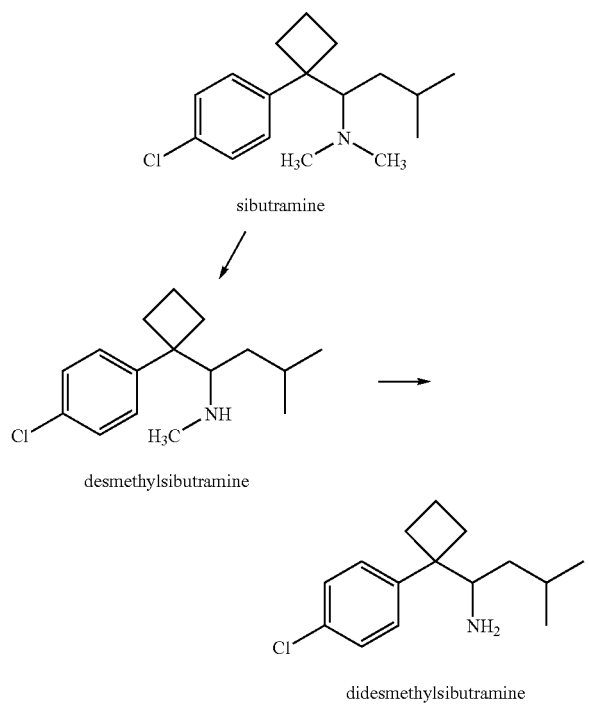

Both didesmethylsibutramine and desmethylsibutramine have interesting and useful biological properties. Each of these sibutramine metabolites can exist as an enantiomeric pair of R and S enantiomers, as shown below in Scheme II, which also exhibit interesting and useful biological properties:

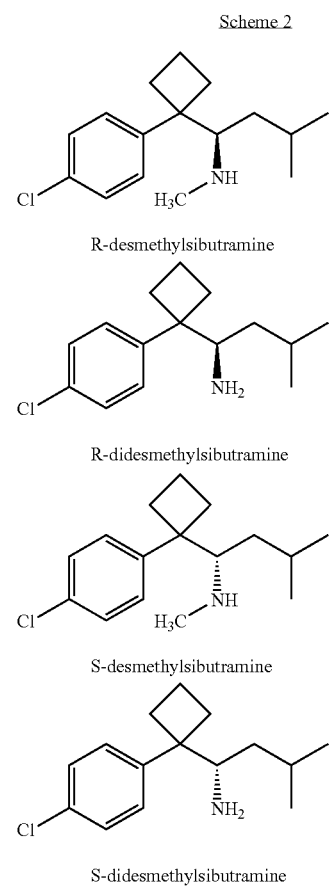

The preparation of enantiomerically pure metabolites of sibutramine and derivatives thereof (e.g., didesmethylsibutramine) has been difficult. Consequently, a need exists for improved methods of synthesis.

Several methods of preparing amine stereoisomers are known in the art. One general method comprises asymmetric addition to an imine, such as by reduction (which adds hydrogen atoms to the carbon and nitrogen atoms at the ends of the C=N double bond) or by reaction with a source of a nucleophile (which adds hydrogen to the nitrogen atom and the nucleophile to the carbon atom). For example, when the source of a nucleophile is a source of a nitrile, such as HCN, the reaction affords an amine stereoisomer in which hydrogen is added to the nitrogen atom and CN to the carbon atom. The nitrile group may then be hydrolyzed to afford an alpha-substituted amino acid stereoisomer.

One such method that has been reported, for example in Liu et al., *J. Am. Chem. Soc.*, 1997, 119, 9913–9914, comprises addition to a sulfinylimine stereoisomer that bears on the sulfinyl group a residue of a hydrocarbyl group, such as p-toluyl or tert-butyl. The resultant sulfinylimine may then be treated with a reagent suitable for the cleavage of a sulfur-nitrogen bond, such as hydrochloric acid, to afford an amine stereoisomer. The sulfinylimine stereoisomers starting materials may be obtained by reacting a carbonyl compound, such as an aldehyde of ketone, with a sulfinamide stereoisomer, such as a p-toluenesulfinamide or tert-butanesulfinanide stereoisomer.

A novel method of preparing amine stereoisomers has now been found that starts with a sulfinylimine that bears on the sulfinyl group a residue of an alcohol, thiol or amine.

According to one aspect, therefore, the present invention provides a method of preparing an amine stereoisomer, which comprises stereoselectively reducing a sulfinylimine that bears on the sulfinyl group a residue of an alcohol, thiol or amine, or reacting a sulfinylimine stereoisomer that bears on the sulfinyl group a residue of an alcohol, thiol or amine with a source of a nucleophile, to afford a sulfinylamine stereoisomer, followed by contacting the sulfinylamine stereoisomer with a reagent suitable for the cleavage of a sulfur-nitrogen bond, to afford an amine stereoisomer.

It will be appreciated that reduction of the sulfinylimine affords a sulfinylamine stereoisomer when the sulfinylimine starting material is a sulfinylimine stereoisomer, or when the reduction is performed using a stereoselective reducing agent. When a sulfinylimine is reduced, hydrogen atoms are added to the nitrogen and carbon atoms of the imine group. When a sulfinylimine stereoisomer is reacted with a source of a nucleophile, a hydrogen atom is added to the nitrogen atom and the nucleophile to the carbon atom. Examples of sources of nucleophiles include nitriles, Grignard reagents and organolithiums.

In one embodiment of the invention, the sulfinylimine is a sulfinylimine stereoisomer. The residue of the alcohol, thiol or amine may also be in stereoisomeric form.

Particular mention is made of sulfinylimines that bear a residue of an alcohol on the sulfinyl group, especially those wherein the residue of the alcohol is a residue of an optionally N-substituted beta-aminoalcohol, thiol or amine, in particular an optionally N-substituted beta-aminoalcohol.

In one embodiment, the N-substituted beta-aminoalcohol, thiol or amine may be represented by the general formula

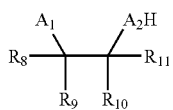

wherein $A_1$ is $R_7N$ or $(R_{7'})R_{7''}N$, $R_7$ represents hydrogen or -L-$R_{7a}$ in which -L- represents a bond, —CO—, —(CO)O—, —(CO)NR$_{7b}$—, —SO—, —SO$_2$—, or —(SO$_2$))O—, each of $R_{7a}$ and $R_{7b}$ independently represents substituted or unsubstituted alkyl, substituted or unsubstituted aralkyl, substituted or unsubstituted heteroalkyl, substituted or unsubstituted aryl or substituted or unsubstituted heteroaryl, and $R_{7'}$ and $R_{7''}$ are as defined for $R_{7a}$, or $R_{7'}$ and $R_{7''}$ together with the nitrogen atom to which they are attached and, optionally $R_8$, form an unsubstituted or substituted heterocyclic group, or $R_{7'}$ together with the nitrogen atom to which it is attached and the carbon atom to which the nitrogen atom is attached forms an unsubstituted or substituted heterocyclic group; $A_2$ is O, S or NR$_{7c}$ in which R$_{7c}$ is substituted or unsubstituted alkyl, substituted or unsubstituted aralkyl, substituted or unsubstituted heteroalkyl, substituted or unsubstituted aryl or substituted or unsubstituted heteroaryl; and each of $R_8$, $R_9$, $R_{10}$ and $R_{11}$ is independently hydrogen, substituted or unsubstituted alkyl, substituted or unsubstituted aralkyl, substituted or unsubstituted heteroalkyl, substituted or unsubstituted aryl or substituted or unsubstituted heteroaryl, or $R_8$ and $R_{11}$ together form a substituted or unsubstituted alkylene or heteroalkylene chain.

By way of illustration, an example of a compound in which $R_{7'}$ and $R_{7''}$ together with the nitrogen atom to which they are attached and, optionally $R_8$, form an unsubstituted or substituted heterocyclic group is quinidine. An example of a compound in which $R_{7'}$ together with the nitrogen atom to which it is attached and the carbon atom to which the nitrogen atom is attached forms an unsubstituted or substituted heterocyclic group is the compound of formula

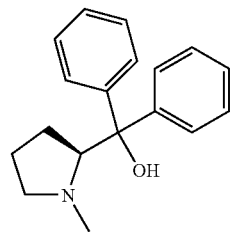

The residue of the alcohol, thiol or amine is preferably a residue of an alcohol ($A_2$ is O).

$R_7$ may represent, for example, —SO$_2$—$R_{7a}$.

Examples of particular values for $R_{7a}$ are (1–6C)alkyl, (6–10C)aryl(1–4C)alkyl or (6–10C)aryl in which any aryl group is unsubstituted or substituted by one, two or three substituents selected independently from halogen, (1–4C)alkyl and (1–4C)alkoxy.

Thus, examples of particular values for $R_7$ are methanesulfonyl and p-toluenesulfonyl.

Examples of particular values for $R_{7'}$ are (1–4C)alkyl groups, such as methyl or butyl.

Examples of particular values for $R_{7''}$ are (1–4C)alkyl groups, such as methyl or butyl.

Examples of particular values where $R_{7'}$, $R_{7''}$ and the nitrogen atom to which they are attached form an unsubstituted or substituted heterocyclic group are pyrrolidine groups that optionally bear one or two methyl substituents, such as pyrrolidinyl, 2-methylpyrrolidinyl and 2,5-dimethylpyrrolidinyl.

Examples of compounds containing groups in which $R_{7'}$, $R_{7''}$, $R_8$, and the nitrogen atom to which they are attached form an unsubstituted or substituted heterocyclic group are quinine, quinidine, cinchonidine, cinchonine, hydroquinine, hydrocinchonidine and ethyl hydrocupreine.

Examples of particular values for $R_8$ are hydrogen, (1–4C)alkyl, such as methyl or ethyl, and phenyl.

Examples of particular values for $R_9$ are hydrogen, (1–4C)allyl, such as methyl or ethyl, and phenyl.

Examples of particular values for $R_{10}$ are hydrogen, (1–4C)alkyl, such as methyl or ethyl, and phenyl.

Examples of particular values for $R_{11}$ are hydrogen, (1–4C)alkyl, such as methyl or ethyl, and phenyl.

Examples of beta-aminoalcohols wherein $A_1$ is $R_7N$ are optionally N-substituted 2-amino-1-phenylpropanols, 2-amino-2-methyl-1-phenylpropanols, 1-amino-1-phenyl-2-propanols, 1-amino-1-phenyl-2-methyl-2-propanols, 1-amino-1-phenyl-2-ethyl-2-butanols, 1-amino-2-indanols, 2-amino-1-indanols, 1-amino-2-hydroxy-1,2,3,4-tetrahydronaphthalenes and 2-amino-1-hydroxytetrahydronaphthalenes.

Examples of beta-aminoalcohols wherein $A_1$ is $(R_{7'})R_{7''}N$ are 2-N,N-dimethylamino-1-phenylpropanol, 2-N,N-dibutylamino-1-phenylpropanol, 2-pyrrolidin-1-yl-1-phenylpropanol, 2-(2-methylpyrrolidin-1-yl)-1-phenylpropanol, 2-(2,5-dimethylpyrrolidin-1-yl)-1-phenylpropanol, 2-N,N-dimethylarino-2-methyl-1-phenylpropanol, (N-methylpyrrolidin-2-yl)diphenylnethanol, 1-pyrrolidin-1-ylindan-2-ol, 3-benzyloxy-2-N,N-dimethylamino-1-phenyl-propan-2-ol, quinine, quinidine, hydroquinine, cinchonidine, cinchonine, hydrocinchonidine or ethyl hydrocupreine.

Structures of representative beta-aminoalcohols are as follows.

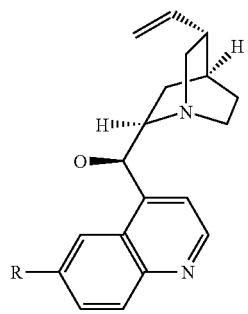

(-)-Quinine, R = OMe
(-)-Cinchonidine, R = H

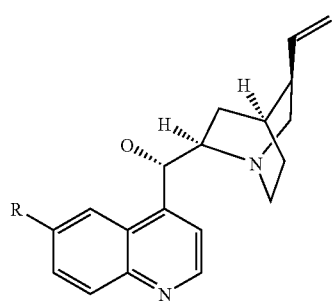

(+)-Quinine, R = OMe
(+)-Cinchonidine, R = H

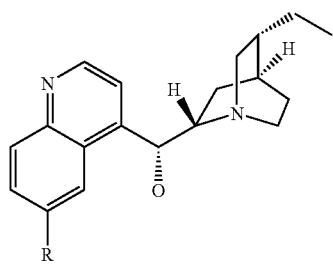

(-)-hydroquinine, R = OMe
(-)-Hydrocinchonidine, R =
Ethyl Hydrocupreine, R = OE

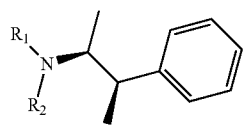

(-)-N-Methyl Ephedrine
$R_1 = R_2 = Me$
$R_1 = R_2 = nBu$

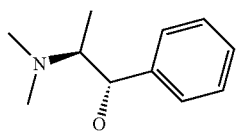

(+)-(1S, 2S)-N-Methyl
-psi-Ephedrine

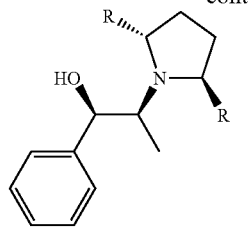

-continued

R = H
R = Me

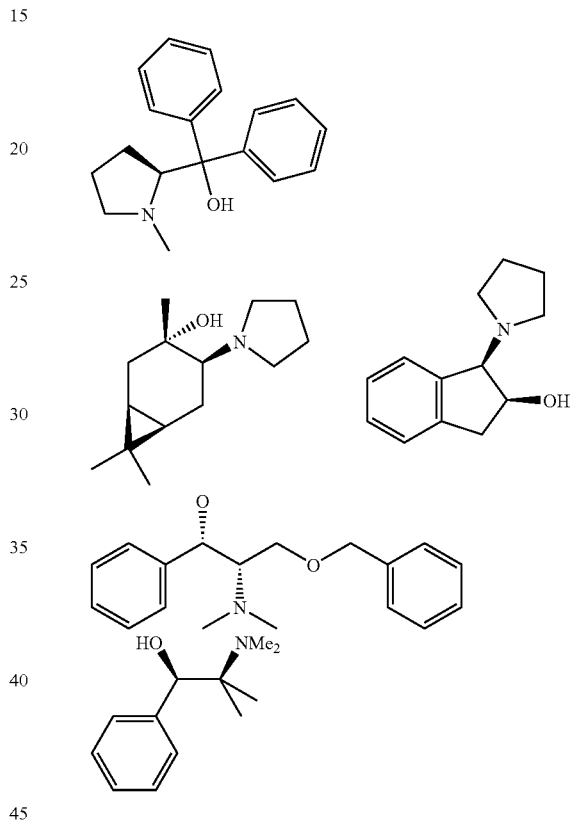

It has been found that especially high stereoselectivity is associated with $A_1$ is $(R_{7'})R_{7''}N$. Accordingly, a preference may be expressed for $A_1$ is $(R_{7'})R_{7''}N$.

Compounds derived from beta-aminoalcohols such as quinine correspond with an alcohol in which $R_{11}$ is unsubstituted or substituted quinolin-4-yl. Accordingly, it is contemplated that alternative examples of particular values for $R_{11}$ are quinolin-4-yl which is unsubstituted or substituted by one or two substituents selected independently from (1–4C)alkyl, (1–4C)alkoxy and halogen.

Sulfinylimines that bear on the sulfinyl group a residue of an alcohol, thiol or amine may be prepared by reacting an iminometal, such as an iminomagnesium chloride, with a compound of formula Z'-SO—R in which Z' represents a leaving atom or group, such as a fluorine, chlorine or bromine atom, and R represents a residue of an alcohol, thiol or amine.

Sulfinylimines in which the sulfinyl group bears a residue of an optionally N-substituted beta-aminoalcohol, thiol or amine may advantageously be prepared by contacting an iminometal, such as an ininomagnesium chloride, with a 1,2,3-oxathiazolidine-S-oxide, 1,2,3-dithiazolidine-S-oxide or 1,2,3-azathiazolidine respectively.

According to a preferred aspect, therefore, the sulfmylirnine used in the method has been prepared by contacting an iminometal with a 1,2,3-oxathiazolidine-S-oxide, 1,2,3-dithiazolidine-S-oxide or 1,2,3-azathiazolidine-S-oxide respectively, especially a 1,2,3-oxathiazolidine-S-oxide, 1,2,3-dithiazolidine-S-oxide or 1,2,3-azathiazolidine-S-oxide stereoisomer (which affords a sulfinylimine stereoisomer in which the sulfinyl group bears a residue of an optionally N-substituted beta-aminoalcohol, thiol or amine also in stereoisomeric form). 1,2,3-Oxathiazolidine-S-oxides, 1,2,3-dithiazolidine-S-oxides and 1,2,3-azathiazolidine-S-oxides may be prepared by reacting respectively an optionally N-substituted beta-aminoalcohol, thiol or amine with a sulfonyl halide, such as thionyl chloride in the presence of an amine base, such as a pyridine derivative.

The 1,2,3-oxathiazolidine-S-oxide, 1,2,3-dithiazolidine-S-oxide or 1,2,3-azathiazolidine-S-oxide may be, for example, a compound of formula 3 or 3'

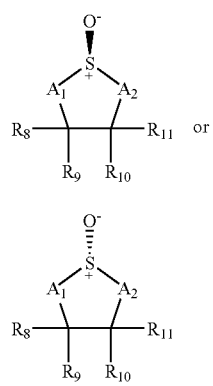

wherein $A_1$ is $R_7N$ or $(R_{7'})R_{7''}N^+ \; Q^-$ in which Q– is an anion, $R_7$ represents hydrogen or -L-$R_{7a}$ in which -L- represents a bond, —CO—, —(CO)O—, —(CO)NR$_{7b}$—, —SO—, —SO$_2$—, or —(SO$_2$)O—, each of $R_{7a}$ and $R_{7b}$ independently represents substituted or unsubstituted alkyl, substituted or unsubstituted aralkyl, substituted or unsubstituted heteroalkyl, substituted or unsubstituted aryl or substituted or unsubstituted heteroaryl, and $R_{7'}$ and $R_{7''}$ are as defined for $R_{7a}$, or $R_{7'}$ and $R_{7''}$ together with the nitrogen atom to which they are attached and, optionally $R_8$, form an unsubstituted or substituted heterocyclic group, or $R_{7'}$ together with the nitrogen atom to which it is attached and the carbon atom to which the nitrogen atom is attached forms an unsubstituted or substituted heterocyclic group; $A_2$ is O, S or NR$_{7c}$ in which $R_{7c}$ is substituted or unsubstituted alkyl, substituted or unsubstituted aralkyl, substituted or unsubstituted heteroalkyl, substituted or unsubstituted aryl or substituted or unsubstituted heteroaryl; and each of $R_8$, $R_9$, $R_{10}$ and $R_{11}$ is independently hydrogen, substituted or unsubstituted alkyl, substituted or unsubstituted aralkyl, substituted or unsubstituted heteroalkyl, substituted or unsubstituted aryl or substituted or unsubstituted heteroaryl, or $R_8$ and $R_{11}$ together form a substituted or unsubstituted alcylene or heteroalkylene chain.

The iminometal may be, for example, a compound of formula 1'

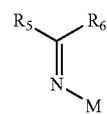

wherein M is CdZ, BaZ, Na, K, MgZ, ZnZ, Li, MnZ, CuZ, TiZ$_3$ or In and Z is an anion.

When the sulfinylamine has been prepared from a sulfinylimine in which the sulfinyl group bears the residue of an optionally N-substituted beta-aminoalcohol, thiol or amine, treatment of the sulfinylamine with a reagent suitable for the cleavage of a sulfur-nitrogen bond, such as an acid, affords as a second reaction product the optionally N-substituted beta-aminoalcohol, thiol or amine. This alcohol, thiol or amine may advantageously be recycled by converting it into 1,2,3-oxathiazolidine-S-oxide, 1,2,3-oxadiathiazolidine-S-oxide or 1,2,3-azathiazolidine-S-oxide. According to a preferred aspect therefore, the method further comprises recovering optionally N-substituted beta-aminoalcohol, thiol or amine, converting this into 1,2,3-oxathiazolidine-S-oxide and reacting this with an iminometal as described hereinabove.

A sulfinylimine may be reduced to a sulfinylamine stereoisomer using any suitable reducing agent. Thus, it will be appreciated that the reducing agent may be any reducing agent capable of reducing a sulfinylimine to a sulfinylamine, provided that if the sulfinylimine is not a sulfinylimine stereoisomer, then the reducing agent is a stereoselective reducing agent. Examples of reducing agents include hydrogen, in the presence of a group VIII metal catalyst, such as palladium on carbon; boranes; hydrogen transfer reagents, such as cyclohexene and formic acid in the presence of palladium on carbon, and hydride-type reducing agents.

Examples of stereoselective reducing agents include asymmetric hydrogenation agents, asymmetric transfer hydrogenation reagents and asymmetric oxazaborolidine agents.

Examples of asymmetric hydrogenation agents are described in Burk M J, Allen J G, Kiesman W F: Highly regio- and enantioselective catalytic hydrogenation of enamides in conjucated diene systems: Synthesis and application of γ,δ-unsaturated amino acids. *J. Am. Chem. Soc* (1998) 120:657–663; Burk M J, Casy G, Johnson N B: A three-step procedure for asymmetric catalytic reductive amidation of ketones. *J. Org. Chem* (1998) 63:6084–6085; hang F-Y, Pai C-C, Chan A S C: Asymmetric synthesis of chiral amine derivatives through enantioselective hydrogenation with a highly effective rhodium catalyst containing a chiral bisaminophosphine ligand. *J. Am. Chem. Soc* (1998) 120: 5808; and Doucet H, Ohkuma T, Murata K, Yokozawa T, Kozawa M, Katayama E, England A F, Ikariya T, Noyori N: trans-[RuCl$_2$(phosphane)$_2$(1,2-diamine)] and chiral trans-[RuCl$_2$(phosphane) (1,2-diamine)]: Shelf-stable precatalysts for the rapid, productive, and stereoselective hydrogenation of ketones. *Angew. Chem. Int. Ed* (1998) 37:1703–1707.

Examples of asymmetric transfer hydrogenation reagents are described in Murata K, Ikariya T, Noyori R: New chiral Rhodium and Iridium complexes with chiral diamine ligands for asymmetric transfer hydrogenation of aromatic ketones. *J. Org. Chem* (1999) 64:2186–2187 and references cited therein.

Examples of asymmetric oxazaborolidine agents are described in Hett R, Senanayake C H, Wald S A: Conformational toolbox of oxazaborolidine catalysts in the enantioselective reduction of α-bromo-ketone for the synthesis of (R,R)-formoterol. *Tetrahedron Lett.* (1998) 39:1705–1708 and references cited therein.

A preferred reducing agent is a hydride type reducing agent, for example an alkali metal (lithium, sodium or potassium) aluminium hydride or borohydride. The aluminium or boron atoms may be unsubstituted or substituted by one, two or three substituents, such as alkyl, alkoxy or aryl group, sodium borohydride, lithium aluminium hydride, lithium borohydride, lithium triethylborohydride, diisobutylaluminium hydride, lithium trimethoxyaluminium hydride or sodium bis(2-methoxy)aluminium hydride. Particular mention may be made of sodium borohydride.

The reduction is conveniently performed at a temperature in the range of from −75 to 25° C. Convenient solvents include halogenated hydrocarbons, such as dichloromethane, ethers, such as diethyl ether, methyl t-butyl ether (MTBE) or tetrahydrofuran and alcohols such as methanol or ethanol. Particular mention may be made of ethers, especially tetrahydrofuran. The reduction with the hydride type reducing agent may be performed in the presence of a Lewis acid, such as boron trifluoride, a titanium tetra(1–4C) alkoxide, such as titanium tetraethoxide, titanium tetrapropoxide, titanium tetraisopropoxide; a titanium tetrahalide, such as titanium tetrachloride; a zirconium tetra(1–4C) alkoxide, such as zirconium tetraethoxide or zirconium tetra-t-butoxide; a zinc dihalide, such as zinc dichloride, or a magnesium dihalide, such as magnesium dibromide. Particular mention may be made of titanium tetra(1–4C)alkoxides, for example used with sodium borohydride.

The reagent suitable for cleavage of a sulfur-nitrogen bond may be, for example, an acid. Examples of acids include hydrohalic acids, such as hydrochloric acid; sulfonic acids, such as p-toluenesulfonic acid; pyridinium sulfonates, such as pyridium-p-toluenesulfonate; Amberlyst H-15, boric acid and acetic acid. Particular mention may be made of hydrochloric acid. The cleavage of the sulfur-nitrogen bond is conveniently performed at a temperature in the range of from −50 to 50° C.

Examples of biologically active amine stereoisomers include the stereoisomers of Alacepril, Benazepril, Benazeprilate, Ceronapril, Cilazapril, Cilazaprilat, Delapril, Enalapril, Enalaprilat, Fasidotril, Fosinopril, Imidapril, Imidaprilat, Libenzapril, Lisinopril, Moexipril, Moexiprilat, Moveltipril, Pentopril, Perindopril, Quinapril, Quinaprilat, Ramipril, Sampatrilat, Spirapril, Spiraprilat, Temocapril, Temocaprilate, Trandolapril, Trandolaprilate, Utibapril, Utibaprilat, Zabicipril, Zabiciprilat, Bucillamine, Penicillamine, Thiamphenicol, Cefprozil, Cephalexin, Cephaloglycin, Cilastatin, Alafosfalin, Ethambutol, Sertraline, Tametraline, Acetylcysteine, Selegiline, Azaserine, Dorzolamide, Colchicine, Dilevalol, Enalapril, Methyldopa, Metaraminol, Acivicin, Melphalan, Ubenimex, Tmsulosin, Tirofiban, Dilevalol, N-dodecyl-N-methylephedrinium, Ofenucine, Tinofedrine, Aceglutamide, l-ephedrine, levopropylhexedrine, (+)- and (−)-Norephedrine, Phenylpropanolamine, Pseudoephedrine, d-farm, (R)- and (S)-Tamsulosin, Dimepheptanol, Lofentanil, Tilidine hydrochloride (+)-trans, Ciramadol, Enadoline, Lefetamine, Spiradoline, (+)-Etoxadrol, Levoxadrol, (R)-Amphetamine, Clobenzorex, Dexfenfluramine, Dextroamphetamine, Etilamfetamine, Fenfluramine, Levofenfluramine, Phenylpropanolamine, Cetirzine, (R)- and (S)-Baclofen, (R)- and (S)-Sibutramine, and pharmaceutically acceptable salts thereof.

In one embodiment, the amine stereoisomer is a compound of formula 5 or 5'

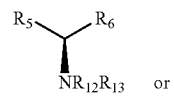

5 or

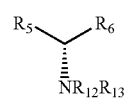

5' or a pharmaceutically acceptable salt, solvate, clathrate, hydrate or prodrug thereof, wherein $R_5$ and $R_6$ are independently substituted or unsubstituted alkyl, substituted or unsubstituted heteroalkyl, substituted or unsubstituted aralkyl, substituted or unsubstituted aryl or substituted or unsubstituted heteroaryl, or $R_5$ and $R_6$ together with the carbon atom to which they are attached form a substituted or unsubstituted cycloalkyl group, and $R_{12}$ and $R_{13}$ together with the nitrogen atom to which they are attached form a heterocycle, or each of $R_{12}$ and $R_{13}$ is independently hydrogen, substituted or unsubstituted alkyl, substituted or unsubstituted aralkyl, or substituted or unsubstituted aryl, and the sulfinylamine stereoisomer is a compound of formula 4 or 4'

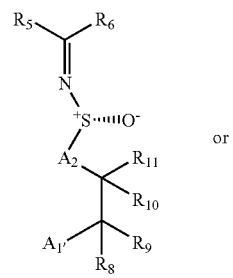

4 or

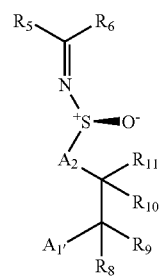

4' wherein $A_{1'}$ represents $R_7N$ or $(R_{7'})R_{7''}N$.

An example of a value for $A_2$ is O.

According to another aspect, the present invention provides a compound of formula

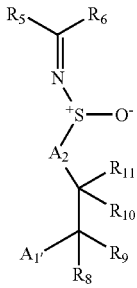

wherein:

R₅ and R₆ are independently substituted or unsubstituted alkyl, substituted or unsubstituted heteroalkyl, substituted or unsubstituted aralkyl, substituted or unsubstituted aryl or substituted or unsubstituted heteroaryl, or R₅ and R₆ together with the carbon atom to which they are attached form a substituted or unsubstituted cycloalkyl group;

A₁ is R₇N or (R₇′)R₇″N;

R₇ represents hydrogen or -L-R₇ₐ in which -L- represents a bond, —CO—, —(CO)O—, —(CO)NR₇ᵦ—, —SO—, —SO₂—, or —(SO₂)O—, each of R₇ₐ and R₇ᵦ independently represents substituted or unsubstituted alkyl, substituted or unsubstituted aralkyl, substituted or unsubstituted heteroalkyl, substituted or unsubstituted aryl or substituted or unsubstituted heteroaryl, and R₇′ and R₇″ are as defined for R₇ₐ, or R₇′ and R₇″ together with the nitrogen atom to which they are attached and, optionally R₈, form an unsubstituted or substituted heterocyclic group, or R₇, together with the nitrogen atom to which it is attached and the carbon atom to which the nitrogen atom is attached forms an unsubstituted or substituted heterocyclic group; A₂ is O, S or NR₇c in which R₇c is substituted or unsubstituted alkyl, substituted or unsubstituted aralkyl, substituted or unsubstituted heteroalkyl, substituted or unsubstituted aryl or substituted or unsubstituted heteroaryl; and each of R₈, R₉, R₁₀ and R₁₁ is independently hydrogen, substituted or unsubstituted alkyl, substituted or unsubstituted aralkyl, substituted or unsubstituted heteroalkyl, substituted or unsubstituted aryl or substituted or unsubstituted heteroaryl, or R₈ and R₁₁ together form a substituted or unsubstituted alkylene or heteroalkylene chain;

A₂ is O, S or NR₇c in which R₇c is substituted or unsubstituted alkyl, substituted or unsubstituted aralkyl, substituted or unsubstituted heteroalkyl, substituted or unsubstituted aryl or substituted or unsubstituted heteroaryl; and each of R₈, R₉, R₁₀ and R₁₁ is independently hydrogen, substituted or unsubstituted alkyl, substituted or unsubstituted aralkyl, substituted or unsubstituted heteroalkyl, substituted or unsubstituted aryl or substituted or unsubstituted heteroaryl, or R₈ and R₁₁ together form a substituted or unsubstituted alkylene or heteroalkylene chain, or a salt thereof.

According to yet another aspect, the present invention provides a compound of formula

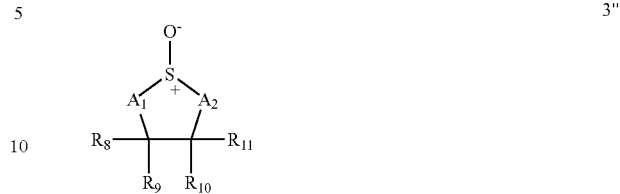

wherein A₁ is (R₇)R₇′N⁺ Q⁻ in which Q– is an anion and each of R₇ and R₇′ independently represents substituted or unsubstituted alkyl, substituted or unsubstituted aralkyl, substituted or unsubstituted heteroalkyl, substituted or unsubstituted aryl or substituted or unsubstituted heteroaryl, or two substituents R₇ together with the nitrogen atom to which they are attached and, optionally R₈, form an unsubstituted or substituted heterocyclic group, or one R₇ substituent together with the nitrogen atom to which it is attached and the carbon atom to which the nitrogen atom is attached form an unsubstituted or substituted heterocyclic group; A₂ is O, S or NR₇c in which R₇c is substituted or unsubstituted alkyl, substituted or unsubstituted aralkyl, substituted or unsubstituted heteroalkyl, substituted or unsubstituted aryl or substituted or unsubstituted heteroaryl; and each of R₈, R₉, R₁₀ and R₁₁ is independently hydrogen, substituted or unsubstituted alkcyl, substituted or unsubstituted aralkyl, substituted or unsubstituted heteroalkyl, substituted or unsubstituted aryl or substituted or unsubstituted heteroaryl, or R₈ and R₁₁ together form a substituted or unsubstituted alkylene or heteroalkylene chain, or a salt thereof.

Compounds of formula 3″ are also useful in a method of preparing sulfinamide stereoisomers, such as the stereoisomers of t-butylsulfinamide.

According to yet another aspect therefore, the present invention provides a method of preparing a sulfinamide stereoisomer, which comprises reacting a compound of formula 3″ as defined hereinabove with a first organometallic reagent of formula R¹M to afford a compound of formula

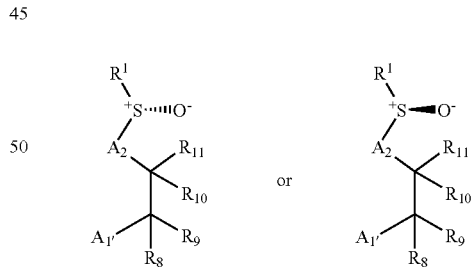

and then either reacting this compound with a second organometallic reagent of formula R²M to afford a sulfoxide stereoisomer of formula

R¹—SO—R² in which R¹ and R² each independently represents an organic group, or with an alkali metal amide to afford a sulfinylamine stereoisomer.

The choice of suitable first and second organometallic reagents and amides, and suitable reaction conditions, will be readily apparent to those skilled in the art. The suitable reagents include Grignard reagents, organolithium reagents, organocopper reagents and organoaluminium reagents. An example of a first or second organometallic reagent is an organomagnesium halide, such as an alkyl or arylmagnesium halide. Examples of an amide are lithium amide and lithium hexamethylenedisilylamide. Examples of uses of these reagents are described in the examples herein. Particularly good results have been obtained using compounds of formula 3" that are derived from quinine.

As used herein, the term "prodrug" means a derivative of a compound that can hydrolyze, oxidize, or otherwise react under biological conditions (in vitro or in vivo) to provide the compound. Examples of prodrugs include, but are not limited to, derivatives of desmethylsibutramine and didesmethylsibutramine that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of desmethylsibutramine and didesmethylsibutramine that comprise —NO, —NO$_2$, —ONO, and —ONO$_2$ moieties. As used herein, prodrugs of didesmethylsibutramine do not include desmethylsibutramine or sibutramine, and prodrugs of desmethylsibutramine do not include sibutramine.

As used herein, the terms "biohydrolyzable carbamate," "biohydrolyzable carbonate," "biohydrolyzable ureide," "biohydrolyzable phosphate" mean a carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically less active or inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "biohydrolyzable ester" means an ester of a compound that either: 1) does not interfere with the biological activity of the compound but can confer upon that compound advantageous properties in vivo, such as uptake, duration of action, or onset of action; or 2) is biologically less active or inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, the term "biohydrolyzable amide" means an amide of a compound that either: 1) does not interfere with the biological activity of the compound but can confer upon that compound advantageous properties in vivo, such as uptake, duration of action, or onset of action; or 2) is biologically less active or inactive but is converted in vivo to the biologically active compound. Examples of biohydrolyzable amides include, but are not limited to, lower alkyl amides, a-amino acid amides, alkoxyacyl amides, and alkylaminoalkylcarbonyl amides.

As used herein, the term "pharmaceutically acceptable salt" refers to a salt prepared from a pharmaceutically acceptable non-toxic inorganic or organic acid. Suitable non-toxic acids include, but are not limited to, acetic, benzenesulfonic, benzoic, camphorsulfonic, citric, ethenesulfonic, flimaric, gluconic, glutamic, hydrobromic, hydrochloric, isethionic, lactic, maleic, malic, mandelic, methanesulfonic, mucic, nitric, pamoic, pantothenic, phosphoric, succinic, sulfiric, tartaric, and p-toluenesulfonic acids. For example, specific pharmaceutically acceptable salts are hydrochloride, maleic acid, and tartaric acid salts.

As used herein and unless otherwise indicated, the term "alkyl" includes saturated monovalent linear, branched, and cyclic hydrocarbon radicals. An alkyl group can include one or more double or triple bonds. It is understood that cyclic alkyl groups comprise at least three carbon atoms.

As used herein and unless otherwise indicated, the term "heteroalkyl" means branched or linear alkyl having from 1 to 8, more preferably from 1 to 4 carbon atoms and including at least one heteroatom, including N, P, O, or S. Examples include, but are not limited to, compounds of the formula:

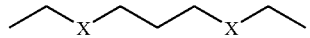

wherein X is O, P, NH, or S.

As used herein and unless otherwise indicated, the term "lower alkyl" means branched or linear alkyl having from 1 to 6, more preferably from 1 to 4 carbon atoms. Examples include, but are not limited to, methyl, ethyl, propyl, isopropyl, isobutyl, and tertiary butyl.

As used herein and unless otherwise indicated, the term "aryl" includes an organic radical derived from an aromatic hydrocarbon by removal of one hydrogen, such as phenyl or naphthyl.

As used herein and unless otherwise indicated, the term "aralkyl" means an aryl substituted with one or linear, branched, or cyclic alkyl groups. Aralkyl moieties can be attached to other moieties through their aryl or alkyl components.

As used herein and unless otherwise indicated, the terms "heterocyclic group" and "heterocycle" include aromatic and non-aromatic heterocyclic groups containing one or more heteroatoms each selected from O, S and N. Non-aromatic heterocyclic groups include groups having only 3 atoms in their ring system, but aromatic heterocyclic groups (i.e., heteroaryl groups) must have at least 5 atoms in their ring system. Heterocyclic groups include benzo-fased ring systems and ring systems substituted with one or more oxo moieties. An example of a 4 membered heterocyclic group is azetidinyl (derived from azetidine). An example of a 5 membered heterocyclic group is thiazolyl, and an example of a 10 membered heterocyclic group is quinolinyl. Examples of non-aromatic heterocyclic groups include, but are not limited to, pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo [4.1.0]heptanyl, 3H-indolyl, quinolizinyl, and substituted derivative thereof. Examples of aromatic heterocyclic groups include, but are not limited to, pyridinyl, methylpyridine analgoues, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzoimidazoles, benzofuranyl, cinnolinyl, indazolyl, indolinyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and substituted derivatives thereof The foregoing groups, as derived from the compounds listed above, may be C-attached or N-attached where such attachment is possible. For instance, a group derived from pyrrole can be pyrrol-1-yl N-attached) or pyrrol-3-yl (C-attached).

As used herein and unless otherwise indicated, the term "heteroaryl" means an aromatic heterocycle.

As used herein and unless otherwise indicated, the term "substituted" as used to describe a compound or chemical moiety means that at least one hydrogen atom of that compound or chemical moiety is replaced with a second chemical moiety. Examples of second chemical moieties include, but are not limited to: halogen atoms (e.g., chlorine, bromine, and iodine); $C_1$–$C_6$ linear, branched, or cyclic alkyl (e.g., methyl, ethyl, butyl, tert-butyl, and cyclobutyl); hydroxyl; thiols; carboxylic acids; esters, amides, silanes, nitrites, thioethers, stannanes, and primary, secondary, and tertiary amines (e.g., —$NH_2$, —$NH(CH_3)$, —$N(CH_3)_2$, and cyclic arines). Preferred second chemical moieties are chlorine, hydroxyl, methoxy, amine, thiol, and carboxylic acid.

As used herein and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of stereoisomer of the compound and less than about 20% by weight of other stereoisomers the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition or compound.

As used herein, compounds encompassed by the term "1,2,3-oxathiazolidine-S-oxides, 1,2,3-dithiazolidine-S-oxides, 1,2,3-azadithiazoline-S-oxides and derivatives thereof" are generally of the formula:

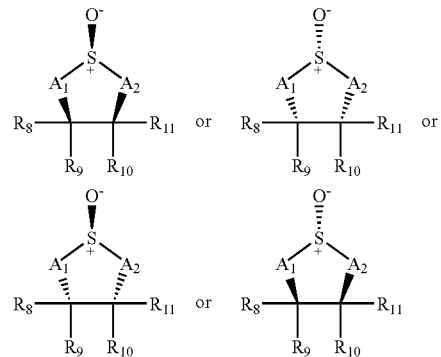

Corresponding iminosulfonates obtainable by reaction of these compounds with an iminometal are of the formula

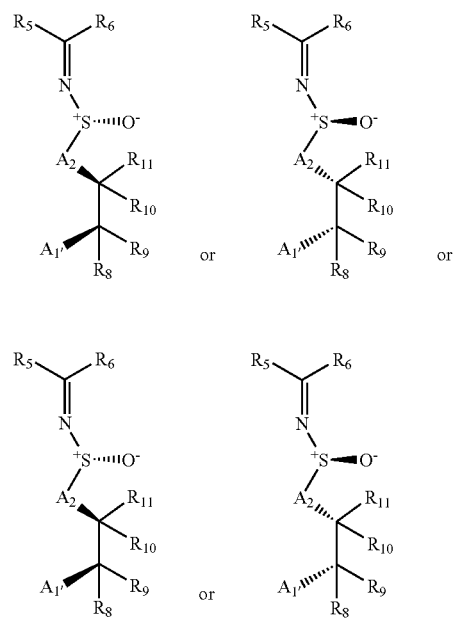

Corresponding optionally N-substituted beta-aminoalcohols, thiols and amines are represented by the formulae:

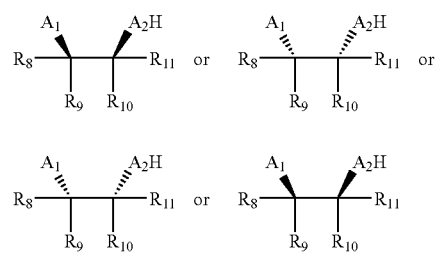

In this embodiment, particular mention is made a method in which $A_2$ is O, $R_5$ and $R_6$ are independently substituted or unsubstituted alkyl, substituted or unsubstituted heteroalkyl, substituted or unsubstituted aralkyl, substituted or unsubstituted aryl or substituted or unsubstituted heteroaryl; the 1,2,3-oxathiazolidine-S-oxide is a compound of the formula 3 or 3'

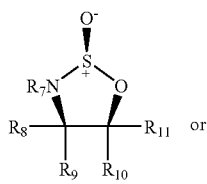

or

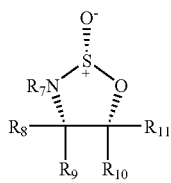

in which $R_7$ represents hydrogen or -L-$R_{7a}$ in which L represents a bond or $SO_2$ and $R_{7a}$ represents substituted or unsubstituted alkyl, substituted or unsubstituted aralkyl, substituted or unsubstituted heteroalkyl, substituted or unsubstituted aryl or substituted or unsubstituted heteroaryl; Z in the iminometal of formula 1' is Cl, Br or I.; and the sulfinylamine stereoisomer is a compound of formula

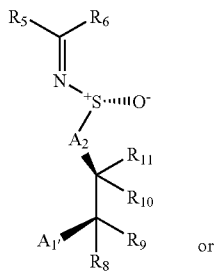

or

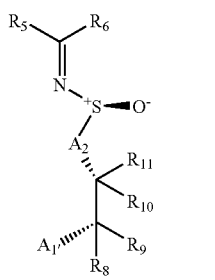

In a preferred embodiment, the term "1,2,3-oxathiazolidine-S-oxides and derivatives thereof" encompasses compounds of the formula:

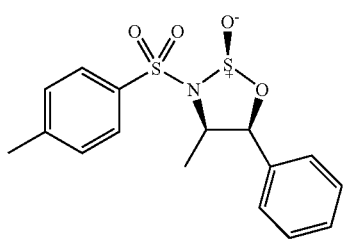

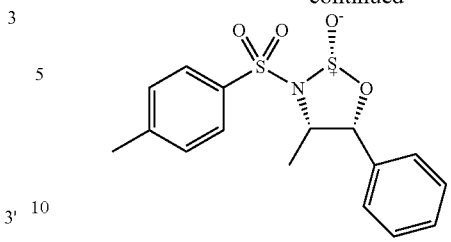

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

A first embodiment of the invention encompasses a method of preparing chiral amines of formulas 5 or 5':

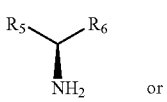

or

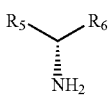

or a pharmaceutically acceptable salt, solvate, clathrate, hydrate, or prodrug thereof, wherein $R_5$ and $R_6$ are independently substituted or unsubstituted alkyl, substituted or unsubstituted heteroalkyl, substituted or unsubstituted aralkyl, or substituted or unsubstituted aryl.

The method of preparing chiral amines of formula 5: or a pharmaceutically acceptable salt, salvate, clathrate, hydrate, or prodnig thereof,

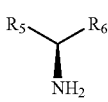

wherein $R_5$ and $R_6$ are independently substituted or unsubstituted alkyl, substituted or unsubstituted heteroalkyl, substituted or unsubstituted aralkyl, substituted or unsubstituted heteroalkyl, or substituted or unsubstituted aryl, comprises contacting a compound of Formula 3:

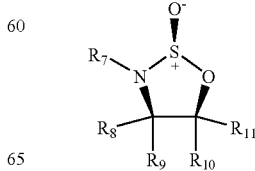

with a compound of formula 1':

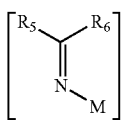
1' wherein under conditions suitable for the formation of a compound of formula 4:

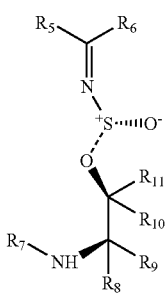
4 followed by hydrogenation and work-up under conditions suitable for the cleavage of a sulfur-nitrogen bond and for the formation of a stereomerically pure amine. In an optional embodiment, the amine compound of formula 5 is treated with an alkylating agent (e.g., alkyl iodide) under conditions suitable for the formation of mono- or di-alkylated amines of formula 5' and 5":

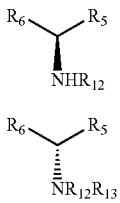
5'
5"

wherein $R_{12}$ and $R_{13}$ is independently substituted or unsubstituted alkyl, substituted or unsubstituted heteroalkyl, substituted or unsubstituted aralkyl, or substituted or unsubstituted aryl.

In another embodiment, the amine compound of formula 5 is optionally treated with a methylating agent (e.g., methyl iodide) under conditions suitable for the formation of mono- or di-methylated amines of formula 6' and 6":

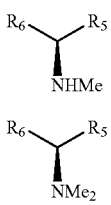
6'
6"

One of ordinary skill in the art will readily recognize that compounds of formula 5' can be prepared by following the above procedure but replacing compound 3 with compound 3':

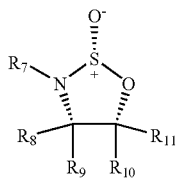
3'

A second embodiment of the invention encompasses a method of preparing a compound of Formula 7:

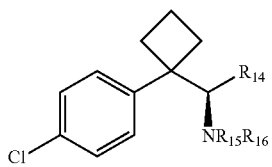
7

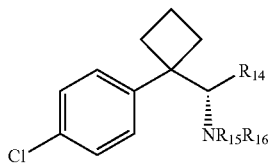
7' or a pharmaceutically acceptable salt, solvate, clathrate, hydrate, or prodrug thereof, wherein $R_{14}$ is substituted or unsubstituted alkyl, substituted or unsubstituted heteroalkyl, substituted or unsubstituted aralkyl, or substituted or unsubstituted aryl, and $R_{15}$ and $R_{16}$ together with the nitrogen atom to which they are attached form a heterocycle, or each of $R_{15}$ and $R_{16}$ is independently hydrogen, substituted or unsubstituted alkyl, substituted or unsubstituted heteroalkyl, substituted or unsubstituted aralkyl, or substituted or unsubstituted aryl, which comprises contacting a compound of Formula 8:

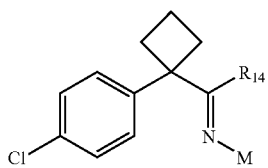
8 wherein M is CdZ, BaZ, Na, K, MgZ, ZnZ, Li, MnZ, CuZ, $TiZ_3$, or In, and Z is Cl, Br, I, aryl, aralkyl, alkoxy, or heterocycle with a compound of formula 3:

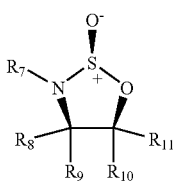

under conditions suitable for the formation of a compound of formula 9:

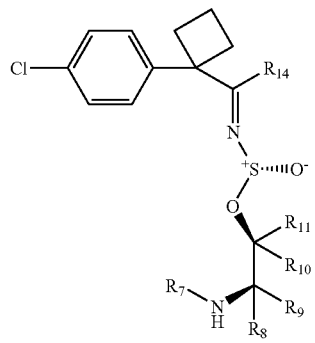

followed by hydrogenation and work-up under conditions suitable for the cleavage of a sulfur-nitrogen bond and for the formation of a stereomerically pure amine of formula 7. In another embodiment, the compound of formula 7 is treated with D-tartaric acid under conditions suitable for the formation of a compound of formula 10:

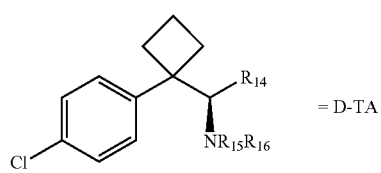

One of ordinary skill in the art will readily recognize that compounds of formula 7' can be prepared by following the above procedure but replacing compound 3 with

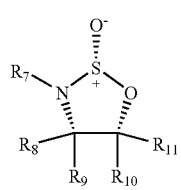

compound 3':

In a preferred method, the compounds of formulas 5, 6, 7, and 10 are stereomerically pure. In another preferred method, the compounds of Formula 5, 6, and 7 are provided as a pharmaceutically acceptable salt. Examples of preferred pharmaceutically acceptable salts include, but are not limited to, acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic salts.

In another preferred method, the reagent capable of cleaving a nitrogen-sulfur bond is an acid. A preferred acid is HCl.

The compound of Formulas 5 or 7, respectively, can be prepared by contacting a compound of Formula 4 or 9:

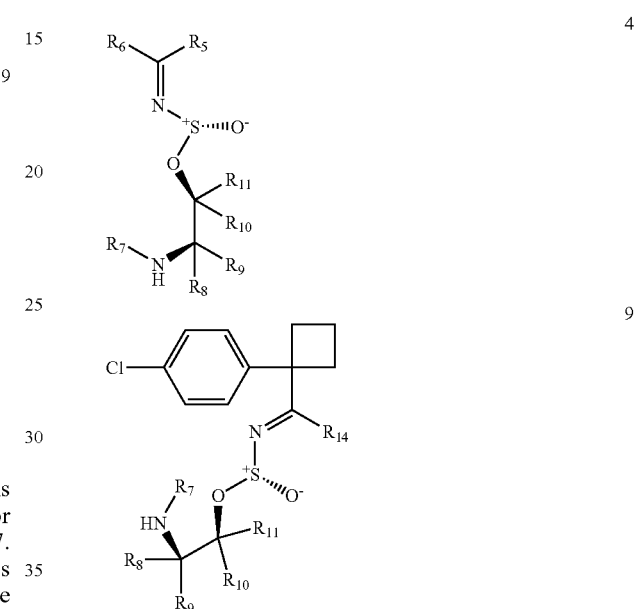

with a Lewis acid and a compound of the formula RM, wherein R is an alkyl, aryl, or arylalkyl and M is Cdz, BaZ, Na, K, MgZ, ZnZ, Li, MnZ, CuZ, TiZ$_3$, or In, and Z is Cl, Br, I, aryl, aralkyl, alkoxy, or heterocycle under conditions suitable for the formation of the compound of Formula 5 or 7.

The compound of Formula 1' can be prepared by contacting a compound of Formula 11:

$R_6$—CN      11 with a compound of formula 12:

$R_5$—M      12 under conditions suitable for the formation of a compound of formula 1':

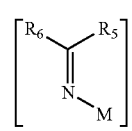

Compounds of formula 12 are generally formed by treating a compound of formula 13:

$R_5$—Hal      13 with a metal or Lewis acid under conditions suitable for the formation of a compound of formula 12. Metals used to generate compounds of formula 12 include, but are not limited to CdZ, BaZ, Na, K, MgZ, ZnZ, Li, MnZ, CuZ, TiZ₃, or In, wherein Z is Cl, Br, aryl, aralkyl, alkoxy, or heterocycle. Examples of Lewis acids include, but are not limited to, $BF_3OEt_2$, $SnCl_4$, $Sc(OTf)_2$, $Al(alkyl)_3$, $Ti(alkyl)_4$, $Ti(alkoxy)_4$, $TiCl_4$, $Zn(OTf)_2$, $Mg(OTf)_2$, $TiHal_k(O\text{-i-Pr})_{4-k}$ (wherein Hal is F, Cl, Br, or I, and k is 1, 2, or 3), and derivatives thereof. Suitable solvents for obtaining compounds 12 include, but are not limited to, dichloromethane, diethyl ether, tetrahydrofuran, benzene, toluene, xylene, hydrocarbon solvents (e.g., pentane, hexane, and heptane), and mixtures thereof. Preferably, the organic solvent is toluene.

The compound of formula 3:

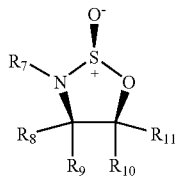

3 can be prepared by treating a compound of formula 2:

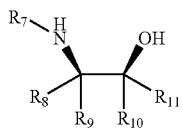

2 with thionyl chloride and a base at low temperature, preferably less than 0° C., more preferably less than −25° C., and most preferably less than −40° C. Preferably, the base is added at a rate such that the reaction-mixture temperature remains within about one to two degrees of the initial reaction-mixture temperature. The base can be added as an organic solution or in undiluted form. Preferably, the base will have a base strength sufficient to deprotonate a proton, wherein the proton has a $pK_a$ of greater than about 15, preferably greater than about 20. As is well known in the art, the $pK_a$ is a measure of the acidity of an acid H-A, according to the equation $pK_a = -\log K_a$, wherein $K_a$ is the equilibrium constant for the proton transfer. The acidity of an acid H-A is proportional to the stability of its conjugate base ⁻A. For tables listing $pK_a$ values for various organic acids and a discussion on $pK_a$ measurement, see March, *J. Advanced Organic Chemistry; Reactions Mechanisms, and Structure*, 4th ed., 1992, pp. 248–272, incorporated herein by reference. Suitable bases include, but are not limited to, alkylmetal bases such as methyllithium, n-butyllithium, tert-butyllithium, sec-butyllithium, phenyllithium, phenyl sodium, and phenyl potassium; metal amide bases such as lithium amide, sodium amide, potassium amide, lithium tetramethylpiperidide, lithium diisopropylamide, lithium diethylamide, lithium dicyclohexylamide, sodium hexamethyldisilazide, and lithium hexamethyldisilazide; and hydride bases such as sodium hydride and potassium hydride. Solvents suitable for reacting compounds 2 with base include, but are not limited, to dimethyl sulfoxide, dichloro-methane, ethers, and mixtures thereof, preferably tetrahydrofuran.

One of ordinary skill in the art will readily recognize that compounds of formula 3':

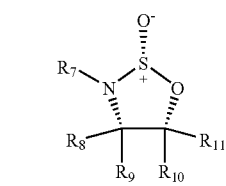

3' can be formed by treating a compound of formula 2':

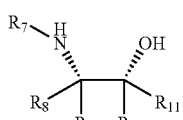

2' with thionyl chloride and base under conditions described above.

In a preferred method, the compound of Formula 3 or 3' is stereomerically pure, as shown below:

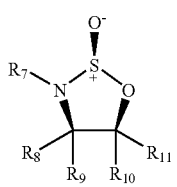

3

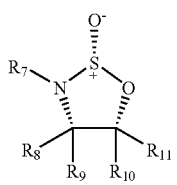

3'

A third embodiment of the invention encompasses a method of preparing a compounds of formula 14 and 14':

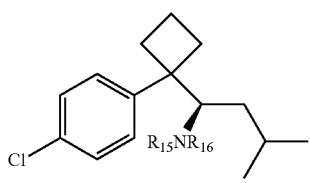

14

-continued

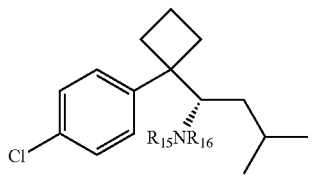

14' and salts, solvates, clathrates, and hydrates thereof, wherein each of $R_{15}$ and $R_{16}$ is described above. In a preferred embodiment, $R_{15}$ and $R_{16}$ are independently hydrogen or alkyl. In a more preferred embodiment, $R_{15}$ and $R_{16}$ are independently hydrogen or methyl. In an even more preferred embodiment, $R_{15}$ and $R_{16}$ are both hydrogen.

The embodiment of the invention encompasses treating a compound of formula 15:

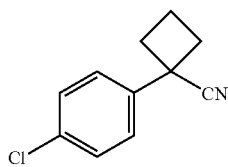

15 with a compound of formula i-BuMg-X, wherein X is a halogen, preferably Br or I, more preferably Br under conditions suitable for the formation of an intermediate of formula:

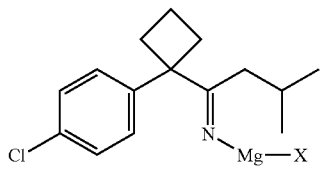

followed by treating with a compound of formula 3:

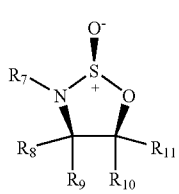

3 under conditions suitable for the formation of a compound of formula 16:

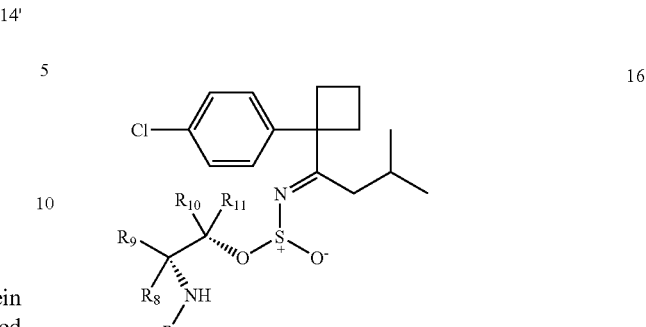

16 and followed by hydrogenation and work-up under conditions suitable for the cleavage of a sulfur-nitrogen bond and for the formation of a stereomerically pure amine of formula 13 or salts, solvates, clathrates, and hydrates thereof. In a preferred embodiment, the compound of formula 3 above has the following structure:

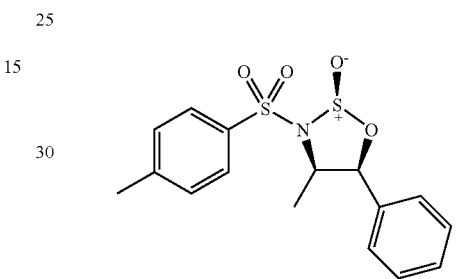

In a preferred method, the compounds of formula 13 are stereomerically pure. In another preferred method, the compounds of Formula 13 are provided as a pharmaceutically acceptable salt, preferably as a tartaric acid salt. In another embodiment, the method encompasses making a compound of formula 14':

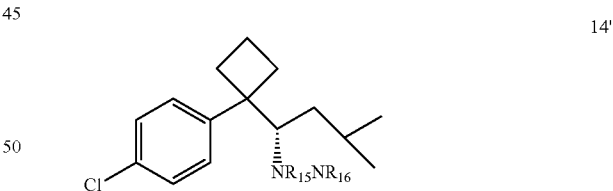

14' under conditions set forth above using a compound of formula 3':

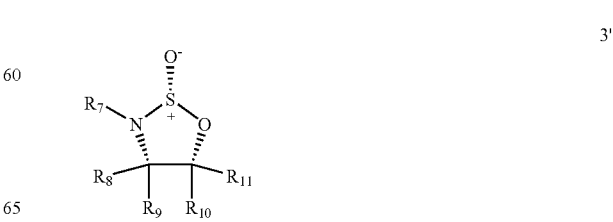

3'

In a preferred embodiment, the compound of formula 3' has the following structure:

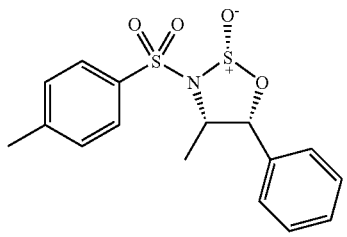

5. EXAMPLES

Sibutramine, desmethylsibutramine, didesmethylsibutramine, and derivatives of each can be readily prepared according to the method represented below in Scheme III. This scheme, like others disclosed herein, is merely representative of a method of the invention, and is not to be construed as limiting its scope in any way.

5.1. Preparation of Stereomerically Pure 1,2,3-oxathiazolidine-S-oxides

The synthesis of stereomerically pure (R)- and (S)-1,2,3-oxathiazolidine-S-oxides is described in Scheme 3.

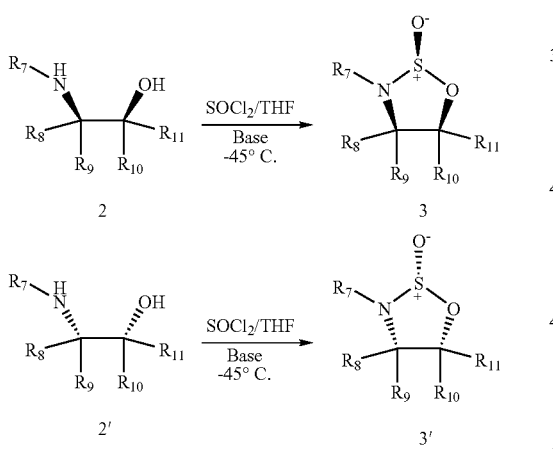

Scheme 3 illustrates the synthesis of $R_s$- and $S_{s-1,2,3}$-oxathiazolidine-S-oxides in stereomerically pure form. Generally, compounds of formula 3 and 3' are formed by contacting compounds of formula 2 or 2', respectively with thionyl chloride at low temperature (e.g., −45° C.) in the presence of a base. The base can be added as an organic solution or in undiluted form. Preferably, the base will have a base strength sufficient to deprotonate a proton, wherein the proton has a $pK_a$ of greater than about 15, preferably greater than about 20. As is well known in the art, the $pK_a$ is a measure of the acidity of an acid H-A, according to the equation $pK_a = -\log K_a$, wherein $K_a$ is the equilibrium constant for the proton transfer. The acidity of an acid H-A is proportional to the stability of its conjugate base $A^-$. For tables listing $pK_a$ values for various organic acids and a discussion on $pK_a$ measurement, see March, *J. Advanced Organic Chemistry; Reactions Mechanisms, and Structure*, 4th ed., 1992, pp. 248–272, incorporated herein by reference. Suitable bases include, but are not limited to, amine bases such as trialkylamine, for example triethylamine and pyridine derivatives, such as pyridine, lutidines, collidines and quinoline. Solvents suitable for reacting compounds 2 with base include, but are not limited to, dimethyl sulfoxide, dichloro-methane, ethers, and mixtures thereof, preferably tetrahydrofuran.

5.2. Preparation of Stereomerically Pure Imines

Stereomerically pure imines can be prepared as shown in Scheme 4.

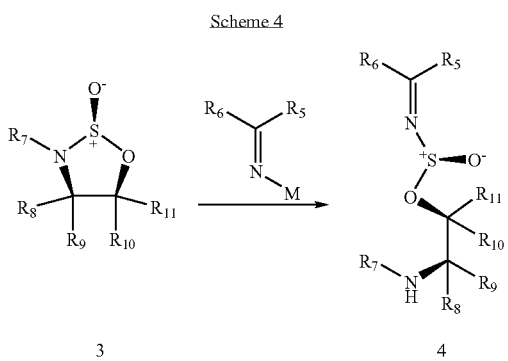

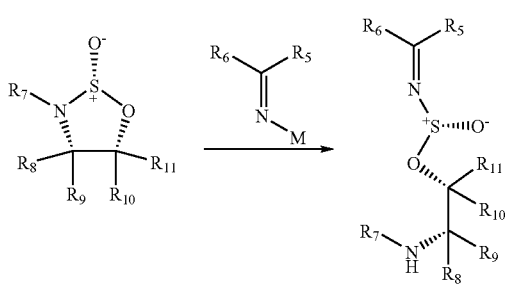

Compounds 4 and 4' can generally be prepared by adding a metal-imine complex to a compound of formula 3 or 3', respectively. In particular, compounds of formula 4 and 4' are generally formed by treating a nitrile with a metal or Lewis acid under conditions suitable for the formation of a metal imine complex. Metals used to generate compounds of formula 1' include, but are not limited to CdZ, BaZ, Na, K, MgZ, ZnZ, Li, MnZ, CuZ, $TiZ_3$, or In, wherein Z is Cl, Br, aryl, aralkyl, alkoxy, or heterocycle. Examples of Lewis acids include, but are not limited to, $BF_3OEt_2$, $SnCl_4$, $Sc(OTf)_2$, $Al(alkyl)_3$, $Ti(alkyl)_4$, $Ti(alkoxy)_4$, $TiCl_4$, $Zn(OTf)_2$, $Mg(OTf)_2$, $TiHal_k(O\text{-}i\text{-}Pr)_{4-k}$ (wherein Hal is F, Cl, Br, or I, and k is 1, 2, or 3), and derivatives thereof. Suitable solvents for obtaining compound 4 and 4' include, but are not limited to, dichloromethane, diethyl ether, tetrahydrofuran, benzene, toluene, xylene, hydrocarbon solvents (e.g., pentane, hexane, and heptane), and mixtures thereof. Preferably, the organic solvent is toluene.

5.3. Reduction of Stereomerically Pure Imines

Stereomerically pure imines can be reduced to stereomerically pure amines as llustrated in Scheme 5.

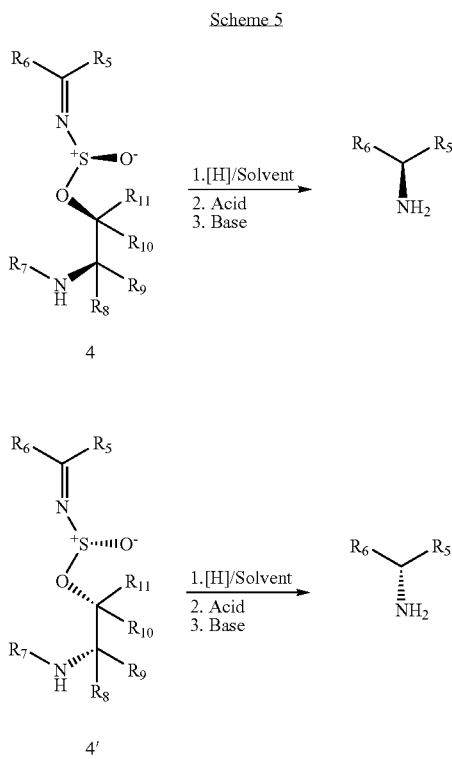

Scheme 5 illustrates the synthesis of stereomerically pure (R)- and (S)-amine compounds. Next, compounds 4 and 4' are first treated with a reducing agent to reduce the imine to a stereomerically pure amine with a suitable reducing agent. A wide variety of reagents are available for reduction of such esters to alcohols, e.g., see M. Hudlicky, *Reductions in Organic Chemistry*, 2nd ed., 1996 pp. 212–217, hereby expressly incorporated herein by reference. Preferably, the reduction is effected with a hydride type reducing agent, for example, sodium borohydride, lithium aluminum hydride, lithium borohydride, lithium triethyl borohydride, diisobutylaluminum hydride, lithium trimethoxyaluminum hydride, or sodium bis(2-methoxy)aluminum hydride. Preferably, the reduction is conducted by adding an organic solution of compounds 4 or 4' to a stirred mixture comprising a reducing agent, preferably sodium borohydride hydride, and an organic solvent. During the addition, the reaction mixture is maintained at a constant temperature within the range of about −20° C. to about 80° C., preferably at about room temperature. Organic solvents suitable for reduction include, but are not limited to, dichloromethane, diethyl ether, tetrahydrofuran or mixtures thereof, preferably tetrahydrofuran. After the addition, the reaction mixture is stirred at a constant temperature within the range of about 0° C. to about −45 ° C., until the reaction is substantially complete as determined by using an appropriate analytical method, preferably thin-layer chromatography or high-performance-liquid chromatography. Then the reaction an acid is added to the reaction mixture to facilitate cleavage of the sulfur-nitrogen bond. The sulfur-nitrogen bond is preferably cleaved with an acid. Suitable cleavage reagents include, but are not limited to, aqueous hydrochloric acid, p-toluenesulfonic acid in methanol, pyridinium-p-toluenesulfonate in ethanol, Amberlyst H-15 in methanol, boric acid in ethyleneglycol-monoethylether, acetic acid in a water-tetrahydrofuran mixture, aqueous hydrochloric acid is preferred. Purification and separation of the stereoisomers (i.e., enantiomers or diastereomers) can be achieved by methods known in the art, for example, conversion to a chiral salt and crystallization, chiral chromatography, or chiral HPLC.

5.4. Preparation of Enantiomericolly Pure (R)-Didesmethylsibutramine

Enantiomerically pure (R)-didesmethylsibutramine can be prepared as shown below in Schemes 6.

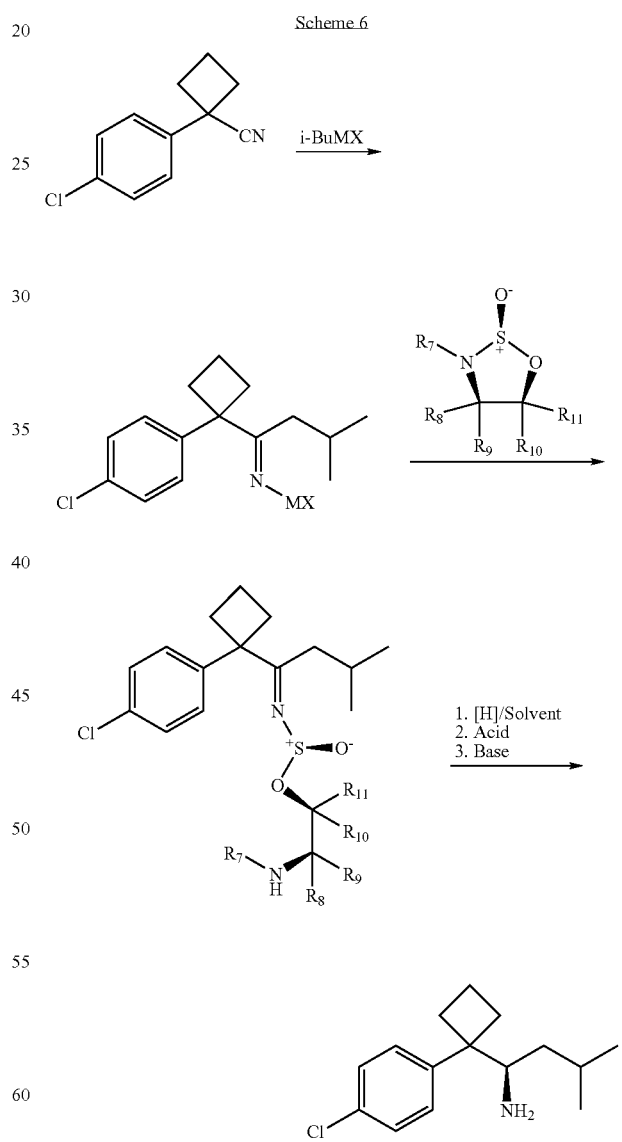

wherein each of $R_7$, $R_8$, $R_9$, $R_{10}$, and $R_{11}$ are defined above.

5.5. Preparation of Enantiomerically Pure (S)-didesmethylsibutramine

Enantiomerically pure (S)-didesmethylsibutramine can be prepared as shown below in Schemes 7.

Scheme 7

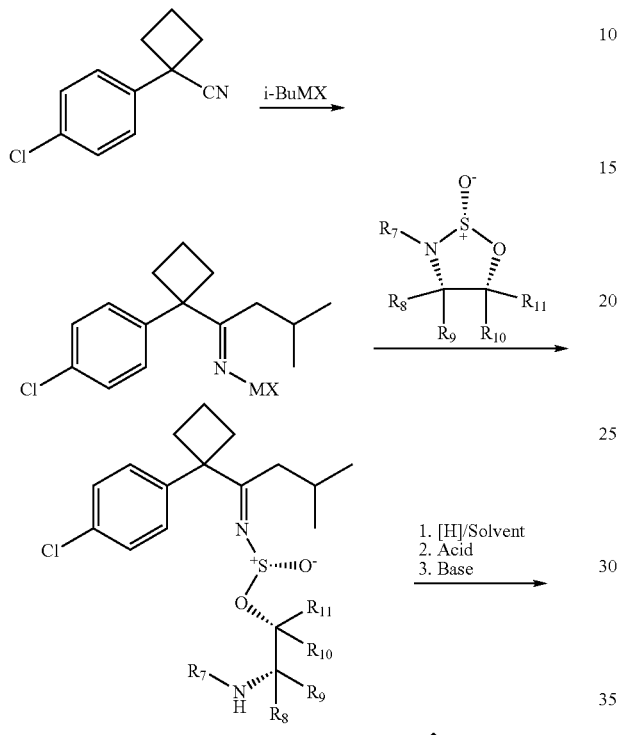

wherein each of $R_7$, $R_8$, $R_9$, $R_{10}$, and $R_{11}$ are defined above.

5.6. Preparation of (R)-{1-[1-(4-chloro-phenyl)-cycloybutyl]-3-methyl-mutylidene}-sulfinamic acid (1S,2R)-1-phenyl-2-(4-methylphenyl sulfonylamino)-propyl ester

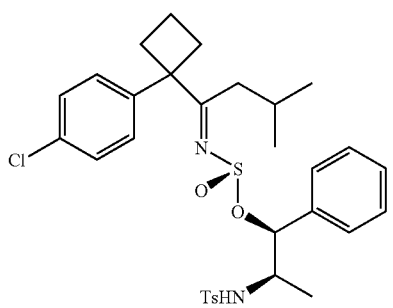

To a 100 mL three-necked flask equipped with a magnetic stir bar, an argon inlet, a thermometer probe and rubber septum, was charged 1-(4-chloro-phenyl)-cyclobutane-carbonitrile (CCBC) (5.0 g, 25.0 mmol, 96%), toluene (20 mL) and isobutyl magnesium chloride (20 mL, 0.9 M in MTBE). The reaction mixture was distilled to the internal temperature of >100° C. and the resulting mixture refluxed for 2 h. After cooling to room temperature, the mixture (8.5 mL) was added slowly to a solution of (2S,4R,5s)-(4-Methyl-5-phenyl-3-(4-methyl phenyl sulfonyl)-[1,2,3]-oxathiazolidine-2-oxide (2.0 g) in THF (14 mL) at −78° C. The mixture was stirred at −78° C. for 4 h, warmed to 10° C. with stirring and the reaction was monitored by TLC. The reaction was quenched by slow addition of saturated aqueous $NaHCO_3$ solution (10 mL) and diluted with ethyl acetate (20 mL). The organic phase was washed with 20% aqueous NaCl solution and dried over $Na_2SO_4$. After evaporation of the organic solvent to dryness, the residue was purified by chromatography using $CH_2Cl_2$/EtOAc (9.6:0.4) as a eluate to yield the title compound (2.8 g, 80%). $^1$H NMR (CDCl$_3$): δ 0.640 (d, J=6.0 Hz, 6H), 1.043 (d, J=6.6 Hz, 3H), 1.660 (b, 1H), 1.835–1.912 (m, 2H), 2.223–2.308 (m, 2H), 2.417 (s, 3H), 2.417–2.536 (m, 2H), 2.733–2.885 (m, 2H), 3.670–3.748 (m, 1H), 5.5.562 (d, J=2.1 Hz, 1H), 5.905 (d, J=9.0 Hz, 1H), 7.125–7.151 (m, 3H), 7.224–7.366 (m, 8H), 7.851 (d, J=8.4 Hz, 2H).

$^{13}$C NMR (CDCl$_3$): δ 15.19, 15.83, 21.61, 22.44, 22.56, 27.87, 32.67, 42.16, 54.27, 56.80, 77.79, 126.10, 127.28, 128.16, 128.45, 128.57, 128.87, 129.77, 133.05, 137.65, 138.24, 141.05, 143.41, 188.55. Anal. $C_{31}H_{37}ClN_2O_4S_2$. Cal: C, 61.93; H, 6.20; N, 4.66; S, 10.67.
Found: C, 61.68; H, 6.12; N, 4.47; S, 10.67.

5.7. (R)-{1-[1-(4-chloro-phenyl)-Cyclobutyl]-3-methyl-butylidene}-sulfinamic acid (1R,2S)-1-(2,4,6-trimethyl-benzenesufonyl amino)-indan-2-yl ester

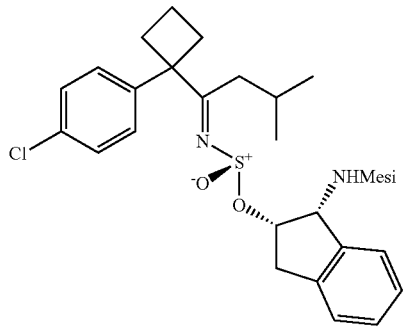

The captioned compound was prepared using the same procedure as described above. The product was obtained in 75% yield. $^1$H NMR (CDCl$_3$): δ 0.645–0.703 (m, 6H), 1.606 (m, 1H), 1.740–1.915 (m, 2H), 2.157–2.257(m, 2H), 2.320 (s, 3H), 814.37 2.715 (s, 6H), 2.832–2.984 (m, 2H), 3.179 (dd, J1=4.64 Hz, J2=16.965 Hz, 1H), 3.359 (d, J=16.84 Hz, 1H), 4.975 (dd, J1=4.85 Hz, J2=9.27 Hz, 1H), 5.395 (d, J=9.03 Hz, 1H), 5.870 (m, 1H), 6.838 (d, J=7.45 Hz, 1H), 6.992 (s, 2H), 7.08–7.15 (m, 1H), 7.18–7.23 (m, 2H), 7.308–7.405 (m, 4H). $^{13}$C NMR (CDCl$_3$): δ15.891, 21.143, 22.625, 23.328, 27.633, 31.995, 32.865, 39.093, 42.406, 56.953, 60.417, 76.335, 124.126, 125.271, 127.436, 128.702, 128.941, 132.215, 132.991, 135.185, 138.960, 139.126, 140.133, 141.675, 142.440, 187.856. Anal: $C_{33}H_{39}ClN_2O_4S_2$. Cal: C, 63.19; H, 6.27; N, 4.47; S, 10.22. Found: C, 63.17; H, 6.21; N, 4.32; S, 9.86.

5.8. Preparatin of Stereomerically Pure Imine Precursors of (R)- and (S)-didesmethylsibutramine Stereomerically pure imine precursors of (R)- and (S)-didesmethylsibutramine can prepared as described in Scheme 8.

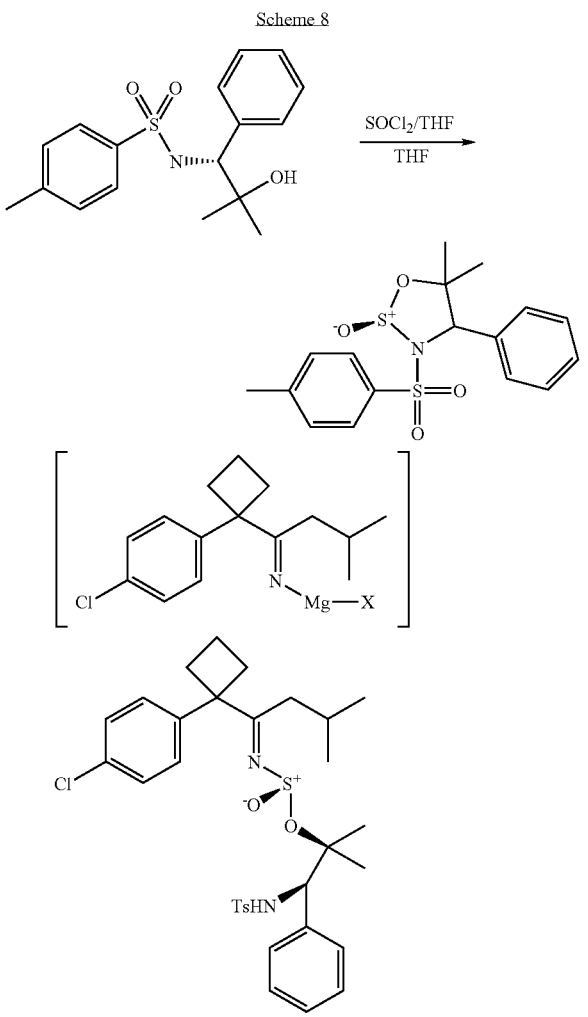

5.8.1. Preparation of (2S,4R)-5,5-dimethyl-4-phenyl-3-(4-methyl phenyl-sulfonyl)-[1,2,3]-oxathiazolidine-2-oxide To a solution of (1R)-N-(2-hydroxy-2-methyl-1-phenylpropyl)-4-methyl-benzene sulfonamide (2.0 g, 6.3 mmol) in THF 8 mL at −45° C. was added SOCl$_2$ (1.12 g, 9.4 mmol), followed by slow addition of pyridine (1.24 g, 12.9 mmol) in THF (8 mL) over a period of 2 h. The reaction was monitored on TLC. The reaction was quenched by addition of saturated aqueous NaHCO$_3$ and the mixture was extracted with EtOAc (30 ml), and organic phase washed with brine (20 mL) and evaporated to dryness. The residue was added hexane (40 mL) and stirred at ambient for 2 h. The precipitate formed was filtered and wet cake washed with hexane to afford the title compound (2.0 g, 87.5%) with 99% de.

5.8.2. Preparation of (R)-{1-[1-(4-chloro-phenyl)-cyclobuthyl]-3-methyl-butylidene}-sulfinamic acid (R)-1,1-dimethyl-2-phenyl-2-(4-methylphenyl-sulfonylamino)-ethyl ester The captioned compound was prepared using the same procedure as Scheme 8 for the preparation of the imine above. The product was obtained in 60% yield. $^1$H NMR (CDCl$_3$): δ 0.586 (d, J=6.4 Hz, 3H), 0.637 (d, J=6.4 Hz, 3H), 1.174 (s, 3H), 1.644 (m, 1H), 1.802 (s, 3H), 1.78–1.85 (m, 2H), 2.08–2.20 9m, 2H), 2.280 (s, 3H), 2.32–2.39 (m, 1H), 2.40–2.50 (m, H), 2.74–2.88 (m, 2H), 4.209 (d, J =9.52, 1H), 6.034 (d, J=9.52, 2H, 6.94–7.14 (m, 7H), 7.22–7.26 (m, 4H), 7.36–7.42 (m, 2H). $^{13}$C NMR (CDCl$_3$): δ 15.924, 21.552, 22.701, 26.861, 26.982, 27.557, 32.056, 33.032, 42.593, 56.694, 66.074, 77.339, 85.431, 126.987, 127.635, 127.885, 128.428, 128.913, 129.095, 129.176, 133.040, 136.799, 137.876, 141.704, 142.727, 186.751. Analytical data: C$_{32}$H$_{39}$ClN$_2$O$_4$S$_2$. Anal: Cal: C, 62.47; H, 6.39; N, 4.55; S, 10.42. Found: C, 62.47; H, 6.25; H, 4.39; S, 10.12.

5.9. Preparation of (2S,4R)-5,5-diethyl-4-phenyl-3-(4-methyl phenylsulfoynl)-[1,2,3]-oxathiazolidine-2-oxide

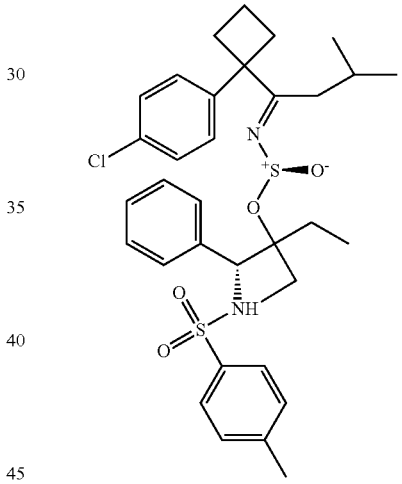

The oxathiazolidine 2-oxide was prepared from (1R)-N-(2-ethyl-2-hydroxy-1-phenyl-butyl)-4-methyl-benzenesulfonamide by following the same procedure in scheme 2, which afforded the product with 88% yield and 99% de. $^1$H NMR (CDCl$_3$): δ0.739 (t, J=7.40 Hz, 3H), 0.968 (t, J=7.42 Hz, 3H), 1.153 (h, J=7.33 Hz, 1H), 1.588 (h, J=7.30 Hz, 1H), 1.860 (dh, J1=3.05, J2=7.30 hz, 2H), 2.310 (s, 3H), 4.806 (s, 3H), 6.98–7.22 (m, 7H), 7.40–7.46 (m, 2H). $^{13}$C NMR (CDCl$_3$): δ7.890, 8.344, 21.692, 28.644, 29.858, 68.610, 103.509, 127.779, 128.078, 128.350, 129.110, 129.418, 133.420, 135.900, 144.365. Anal: C$_{19}$H$_{23}$NO$_4$S; Cal: C, 57.99; H, 5.89; N, 3.56; S, 16.30. Found: C, 58.10; H, 5.73; N, 3.43, S, 16.28.

5.10. Preparation of (R)-{1-[1-(4-chloro-phenyl)-cyclobutyl]-3-methyl-butylidene}-sulfinamic acid (1R)-2-ethyl-1-[phenyl-(4-methyl phenyl sulfonylamino)-methyl]-propyl ester The captioned compound was prepared using the same procedure as Scheme 8 for the preparation of the imine above. The compound was afforded in 90% yield. $^1$H NMR (CDCl$_3$): δ 0.62–0.78 (m, 9H), 1.07 (t, J=7.32 Hz, 3H), 1.14–1.1.28 (m 1H), 1.33–1.47 (m, 1H),1.72 (b, 1H), 1.78–1.90 (m, 2H), 2.02–2.16 (m, 2H), 2.18–2.24 (m, 1H), 2.25 (s, 3H), 2.30–2.60 (m, 3H), 2.74–2.86 (m, 2H), 4.42 (d, J=10.5 Hz, 1H), 6.49 (d, J=10.26 Hz, 1H), 6.87–6.93 (m, 2H), 6.98–7.12 (m, 4H), 7.14–7.20 (m, 2H), 7.24 (s, 3H), 7.30–7.36 (m, 2H). $^{13}$C NMR (CDCl$_3$): δ 7.692, 8.849, 15.910, 21.518, 22.736, 25.669, 27.660, 27.923, 31.957, 33.054, 42.676, 56.814, 61.568, 92.458, 126.880, 127.337, 127.786, 128.434, 128.887, 129.021, 129.708, 133.047, 136.506, 138.210, 141.754, 142.369, 187.15. Anal: C$_{34}$H$_{43}$ClN$_2$O$_4$S$_2$; Cal: C, 63.48; H, 6.74; N, 4.35; S, 9.97. Found: C, 63.10; H, 6.76; N, 4.04, S, 9.95.

5.11. (R)-{1-[1-(4-chloro-phenyl)-cyclobutyl]-pentylidene}-sulfinamic acid (1S,2R)-1-phenyl-2-(4-methyl phenyl sulfonylamino)-propyl ester

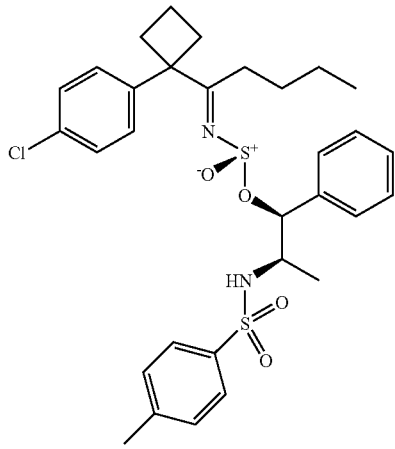

The captioned compound was prepared using the same procedure as Scheme 8 for the preparation of the imine above except that n-butyl magnesium chloride was used. The compound was afforded 60% yield. $^1$H NMR (CDCl$_3$): δ 0.680 (t, J=6.59 Hz, 3H), 0.949–1.150 (m, 6H), 1.700 (s, 1H), 1.857–1.951 (m, 2H), 2.180–2.358 (m, 2H), 2.432 (s, 3H), 2.430–2.544 (m, 2H), 2.720–2.920 (m, 2H), 3.660–3.770 (m, 1H), 5.574 (d, J=2.19 Hz, 1H), 5.886 (d, J=9.28 Hz, 1H), 7.099–7.130 (m, 2H), 7.256–7.362 (m, 9H), 7.851 (d, J=8.30 Hz, 2H). $^{13}$C NMR (CDCl$_3$): δ13.513, 15.431, 15.921, 21.828, 23.196, 31.604, 32.041, 32.199, 33.312, 54.393, 56.780, 77.736, 126.268, 127.518, 128.388, 128.615, 128.684, 129.137, 129.982, 133.385, 137.869, 138.464, 141.142, 143.643, 189.997. Anal: C$_{31}$H$_{37}$ClN$_2$O$_4$S$_2$; Cal: C, 61.93; H, 6.20; N, 4.66; S, 10.67. Found: C, 61.97, H, 6.12; N, 4.61; S, 10.30.

5.12. Asymmetric Synthesis of (R)-DDMS Via Reduction of Imine (R)-Didesmethylsibutramine can be prepared by reduction of the imine as described in Scheme 9.

Scheme 9

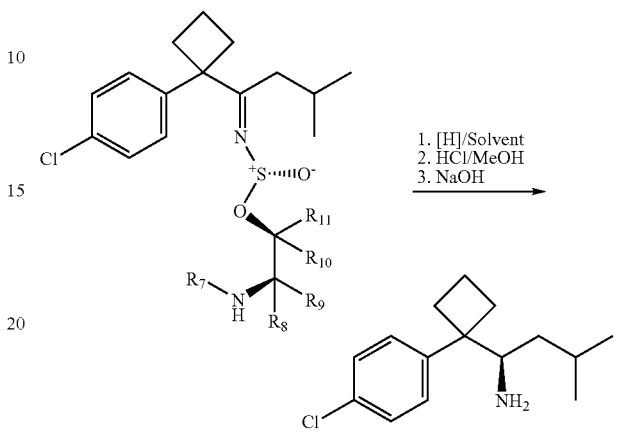

5.12. a. Reduction with NABH$_4$ in the Presence of Titanium Lewis acid

To a two necked round bottomed flask contained a magnetic stirring bar, and temperature probe and an argon outlet was charged the imine (0.1 g, 0.167 mmol, 1.0 eq), THF (3 mL) and Ti(OEt)$_4$ (0.076 g, 2.0 eq), and the mixture was stirred at ambient temperature for 1 h. The mixture was then cooled to −45° C. and NaBH$_4$ (0.025 g, 4.0 eq) was added. After stirred for 3 h, the reaction mixture was warmed slowly up to −10° C.–15° C. and the reaction monitored on TLC. HCl/MeOH (4.0 mL, 4M) was added slowly to quench the reaction and the resulting mixture was stirred at r.t for 3 h. The mixture was cooled to 0° C. and NaOH (5.0 M) was added to a pH>11 and diluted with EtOAc (20 mL). The organic phase was washed with brine (5 mL) and evaporated to dryness. The residue was analyzed on HPLC for yield and ee.

5.13. The Results for the Reduction of Imines using phenyl Oxathiazolidine Chiral Auxiliary Stereomerically pure imines derived from a phenyl-oxathiazolidine chiral auxiliary can be reduced to stereomerically pure didesmethylsibutramne by the reaction conditions described below.

Scheme 10

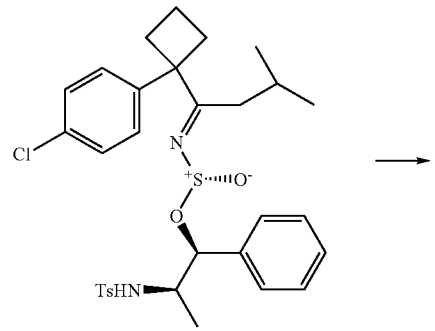

-continued

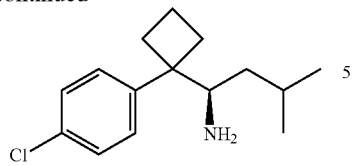

To a two necked round bottomed flask contained a magnetic stirring bar, and temperature probe and an argon outlet was charged the imine (1.0 eq), the solvent and the mixture was cooled to the reaction temperature. Then reducing reagent was added under stirring. The reaction was monitored on TLC and worked up by following the above procedure.

Scheme 11

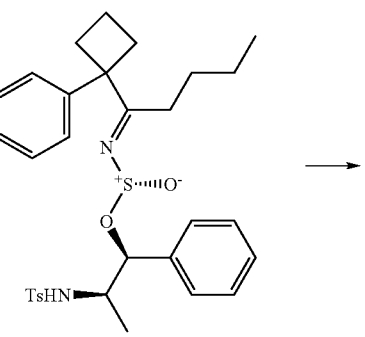

| Entry | Reducing reagents and reaction condition | (R)/(S) | Yield (HPLC analysis) |
|---|---|---|---|
| 1 | NaBH$_4$/THF/−45° C.–0° C. | 80:20 | 97% |
| 2 | NaBH$_4$/MeOH/−45° C.−−20° C. | 72:28 | 95% |
| 3 | NaBH$_4$CH$_3$CN/H$_2$O/0° C. | 66:34 | 98% |
| 4 | NaBH$_4$/THF/MgBr$_2$.OEt$_2$ (No reaction) | | |
| 5 | NaBH$_4$/THF/MgBr$_2$.OEt$_2$/MeOH)/−45° C.–0° C. (No reaction without MeOH) | 64.5:35.5 | 65% |
| 6 | NaBH$_4$/Ti(OPr)$_4$/THF/−45° C.−−20° C. | 85.8:14/8 | 80% |
| 7 | NaBH$_4$/THF/Ti(O$^i$Pr)$_4$/−45° C.−−30° C. | 88:12 | 95% |
| 8 | NaBH$_4$/THF/Ti(OEt)$_4$/−45° C.−−30° C. | 85:15 | 95% |
| 9 | NaBH$_4$/THF/BF$_3$ −45° C.–0° C. | 64:36 | 75% |
| 10 | NaBH$_4$/THF/Zr(OBu-t)$_4$/−45° C.–0° C. | 80:20 | 95% |
| 11 | NaBH$_4$/THF/Zr(OEt)$_4$/−45° C.–10° C. | 82:18 | 95% |
| 12 | NaBH$_4$/THF/TiCl$_4$/−45° C. | 60:40 | 70% |
| 13 | NaBH$_4$/THF/ZnCl$_2$/−45° C.–r.t | 77:33 | 95% |
| 14 | LiBH$_4$/THF/−78° C.−−30° C. | 51:49 | 95% |
| 15 | BH$_3$/THF/−78° C.−−10° C. | 32:68 | 75% (isolated) |
| 16 | 9-BBN/THF/0° C. | 84:16 | 80% |
| 17 | Catecholborane | 49:51 | 96% |
| 18 | L-Selectride | 43:57 | <5% |
| 19 | K-Selectride | 46:54 | <5% |
| 20 | DIBAL/THF/−45° C.−−30° C. | 76:24 | 70% |
| 21 | DIBAL/THF/ZnCl$_2$/−45° C.−−0° C. | 79:21 | 75% |
| 22 | NaBH$_4$/Ti(OPr)$_3$Cl/THF/−45° C.–r.t | 68:32 | 5% |
| 23 | NaBH(OMe)$_3$/THF//−45° C.−−15° C. | 71:29 | 96% |
| 24 | Red-Al/THF/−45° C. | 75:25 | 85% |
| 25 | Na(OAc)$_3$BH/THF (No reaction) | | |
| 26 | NaBH$_3$CN/THF/r.t (No reaction with MeOH, or AcOH, or Ti(OEt)$_4$ | | |
| 27 | Me$_4$NBH(OAc)$_3$/THF/r.t (No reaction with MeOH, or AcOH, or Ti(OEt)$_4$ | | |

5.13. a. Solvent Effect of the Stereoselectivity

| Entry | Reducing reagents and reaction condition | (R)/(S) | Yield (HPLC analysis) |
|---|---|---|---|
| 1 | NaBH$_4$/Ti(OEt)$_4$/THF/r.t | 82:18 | 93% |
| 2 | NaBH$_4$/Ti(OEt)$_4$/MeOH/r.t | 60:40 | 75% |
| 3 | NaBH$_4$/Ti(OEt)$_4$/EtOH/r.t | 72.5:27.5 | 95% |
| 4 | NaBH$_4$/Ti(OEt)$_4$/MTBE/r.t | 83:17 | 78% |

5.14. Synthesis of 1-[1-(4-chloro-phenyl)-cyclobutyl]-pentylamine

Stereomerically pure 1-[1-(4-chloro-phenyl)-cyclobutyl]-pentylamine can be obtained from a phenyl-oxathiazolidine chiral auxiliary by the reaction conditions described below.

-continued

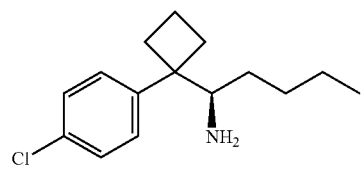

| Entry | Reducing reagents and reaction condition | (R)/(S) | Yield (HPLC analysis) |
|---|---|---|---|
| 1 | NaBH$_4$/Ti(OPr$^i$)$_4$/THF/−45° C. | 88:12 | 85% |

5.15. Synthesis of (R)-didesmethylsibutramine using indan-2-yl chiral auxiliary Stereomerically pure didesmethylsibutramine can be obtained from a stereomerically pure indan-2yl-sulfinyl chiral auxiliary by the reaction conditions described below.

Scheme 12

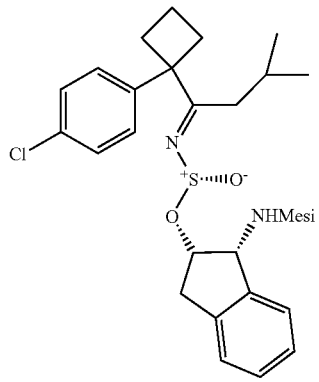

| Entry | Reducing reagents and reaction condition | (R)/(S) | Yield (HPLC analysis) |
|---|---|---|---|
| 1 | NaBH$_4$/THF/Ti(OiPr)$_4$/−45° C.−−10° C. | 79:21 | 87% |
| 2 | NaBH$_4$/THF/Ti(OEt)$_4$/−45° C.−−10° C. | 83.3:16.7 | 95% |
| 3 | NaBH(Oac)3/THF | | No reaction |

5.16. Synthesis of (R)-didesmethylsibutramine using dimethyl oxathiazolindine chiral auxiliary Stereomerically pure didesmethylsibutramine can be obtained from a stereomerically pure dimethyl-sulfinyl chiral auxiliary by the reaction conditions described below.

Scheme 13

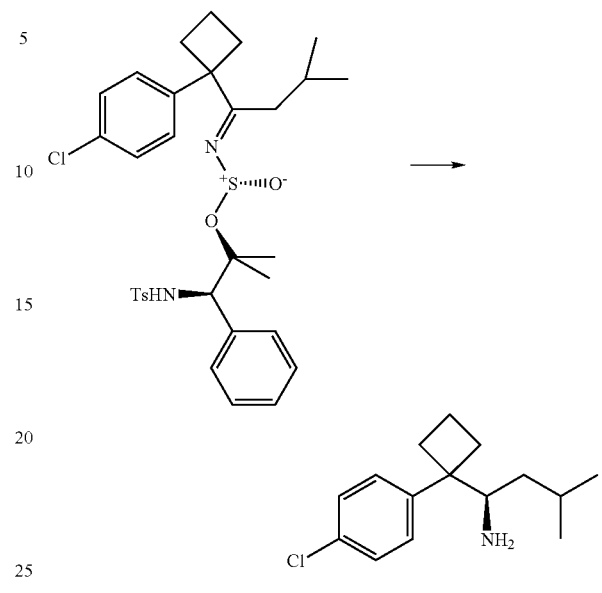

| Entry | Reducing reagents and reaction condition | (R)/(S) | Yield (HPLC analysis) |
|---|---|---|---|
| 1 | NaBH$_4$/THF//−20° C.−−5° C. | 89:11 | 90% |
| 2 | NaBH$_4$/THF/Ti(O$^i$Pr)$_4$/−45° C.−−5° C. | 94:6 | 80% |
| 3 | NaBH$_4$/THF/Ti(OPr)$_4$/−45° C.−−10° C. | 94.2:5.8 | 80% |
| 4 | NaBH$_4$/THF/Ti(OEt)$_4$/−15° C. | 95:5 | 95% |

5.17. Synthesis of (R)-didesmethylsibutramine using diethyl oxathiazolindine chiral auxiliary Stereomerically pure didesmethylsibutramine can be obtained from a stereomerically pure diethyl-sulfinyl chiral auxiliary by the reaction conditions described below.

Scheme 14

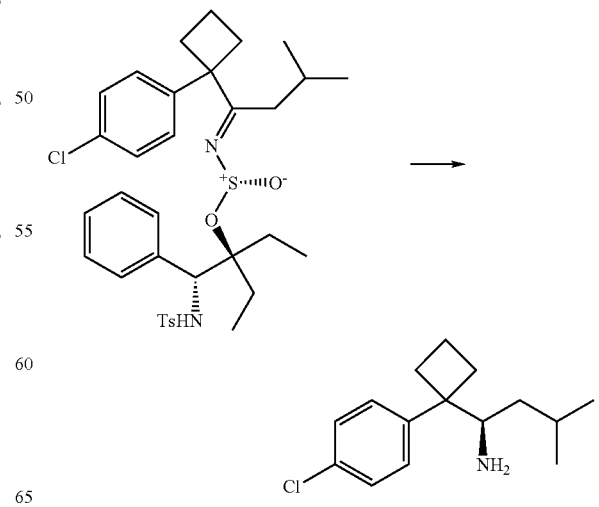

| Entry | Reducing reagents and reaction condition | (R)/(S) | Yield (HPLC analysis) |
|---|---|---|---|
| 1 | NaBH$_4$/THF/Ti(OEt)$_4$/–15° C. | 87:13 | 95% |
| 2 | NaBH$_4$/THF/Ti(O$^i$Pr)$_4$/–45° C.—–15° C. | 88:12 | 90% |

5.18. One Pot Procedure for the Asymmetric Synthesis of (R)-DDMS-D-TA

The one-pot asymmetric synthesis of stereomerically pure D-tartaric acid salt of (R)-didesmethylsibutramine is described below.

Scheme 15

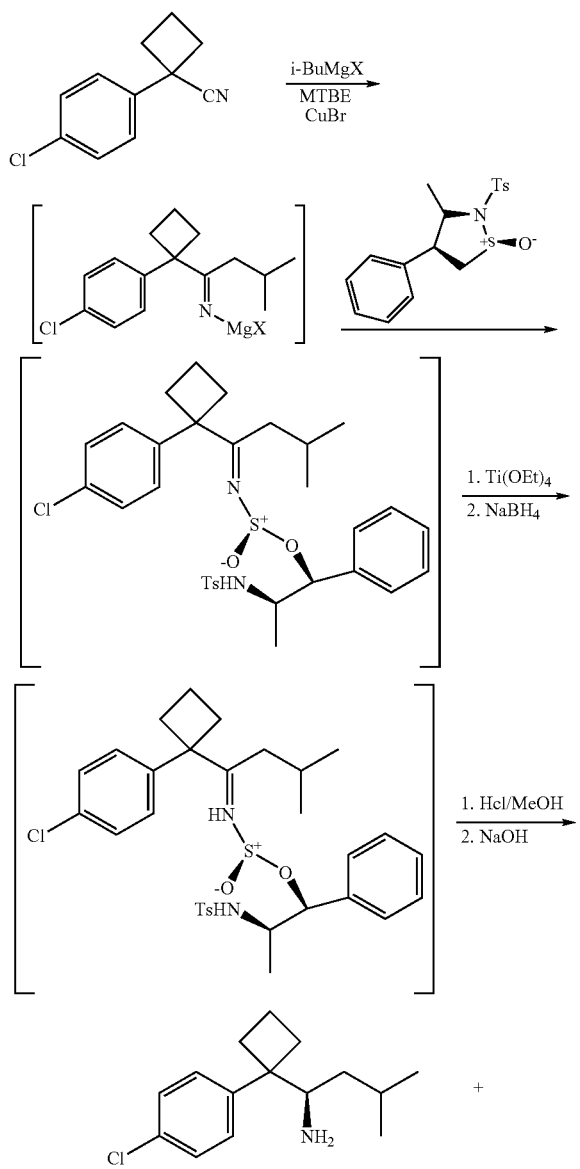

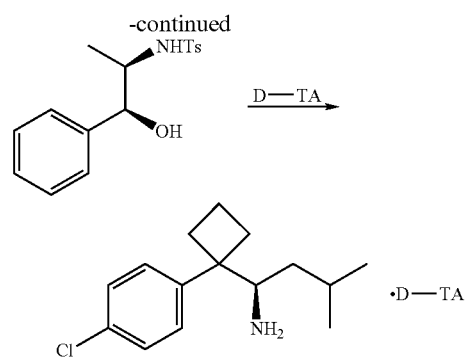

To a 100 mL three-necked flask equipped with a magnetic stir bar, an argon inlet, a thermometer probe and rubber septum, was charged 1-(4-chloro-phenyl)-cyclobutanecarbonitrile (CCBC) (8.0 g, 41.9 mmol (96%)) and CuBr (0.12 g, 2%). After purging the flask with argon for 10 min, MTBE (15 mL) and iBuMgCl (68 mL, 0.61 mol in MTBE) were added and the reaction mixture was refluxed for 4–6 h. The reaction was monitored on HPLC for the disappearance of CCBC. The reaction mixture was cooled to ambient temperature and added drop-wise to the solution of (2S,4R,5S)-4-methyl-5-phenyl-3-(4-methyl phenyl-sulfonyl)-[1,2,3]-oxathiazolidine-2-oxide (15.0 g, 42 mmol) in THF (100 mL) in a 500 mL round-bottomed flask at –78° C. The reaction mixture was stirred for 4 h and warmed up to 10° C. under stirring. The reaction was monitored on TLC for the disappearance of 1-[1-(4-chloro-phenyl)-cyclobutyl]-3-methyl-butylideneamine. Then the reaction mixture was cooled to 0° C. and aqueous ammonium acetate (30%, 50 mL) was added, follows by MTBE (200 mL) and warmed up to ambient temperature. The organic phase was washed with 30% KHCO$_3$ (50 mL) and 20% NaCl (50 mL) and polish filtered through two layers of filter paper. After the resulting organic phase was distilled under reduced pressure to about 50 mL (KF=0.58%), anhydrous THF (80 mL) and Ti(OPr$^i$)$_4$ were added and the mixture was stirred at ambient temperature for 1 h and cooled to –45° C. NaBH$_4$ (6.4 g, 168 mmol) was added in one portion and the mixture was stirred for 6 h and warmed up to –20° C. and the reaction was monitored on TLC for the disappearance of starting material. To the reaction mixture was slowly added aqueous HCl dissolved in MeOH (60 mL, 4M) and the mixture was warmed to ambient temperature and stirred for 3 h. After the mixture was cooled to 0° C., NaOH (5 M) was added slowly to pH ~12 for the solution, the mixture was diluted with toluene (200 mL), and was distilled under reduced pressure to remove the low boiling point solvents. The organic phases were allowed to separate for 20 min and the organic phase was washed twice with aqueous NaCl (50 mL, 20%). The mixture was heated to 60–70° C. and D-tartaric acid (6.3 g) in water (13 ml) and acetone (6 mL) was added slowly. The mixture was distilled under azeotropic condition until the internal temperature reached >95° C. The mixture was then cooled to ambient temperature and stirred for 1 h. The slurry formed was filtered and the wet cake was washed with toluene (30 mL×2) and MTBE (30 mL) and dried at 45° C. for 24 h under reduced pressure to afford the (R)-DDMS.D-TA with 85% yield and 70% ee.

5.18. a. Recovery of (1S,2R)-norephedrine N-tosylate

The above mother liquor was vacuum distilled to about 60 mL and water (50 mL) was added. The resulting mixture was distilled until all the internal temperature reached to ~100° C. and mixture was stirred. Heptane (40 mL) was added and the mixture was stirred to ambient temperature while a nice slurry was formed. The slurry was filtered and the wet cake was washed with water (20 mL) and heptane (30 mL) and dried at 45° C. under reduced pressure to afford 12.5 g (1S,2R)-norephedrine N-tosylate (89.5%).

5.19 Preparation of Sulfoxide and SulfonylAMINE Stereoisomers

Tert-Butylsulfonylquinine (TBSOQ) was isolated in 92% yield, and great than 99% d.e. when (−)-Quinine was used as the chiral auxiliary, and tert-butylmagnesium chloride was used as the first nucleophile ($R^1M$). Displacement of the auxiliary with a second nucleophile ($R^2M$) such as alkyl Grignard reagent, or Aryl diethylaluminium provided the enantiomeric enriched sulfoxides. When TBSOQ was treated with amide anions such as lithium amide in liquid ammonia or lithium bis(trimethylsily)amide in solvent such as THF afforded the enantiomeric enriched sulfinylamides.

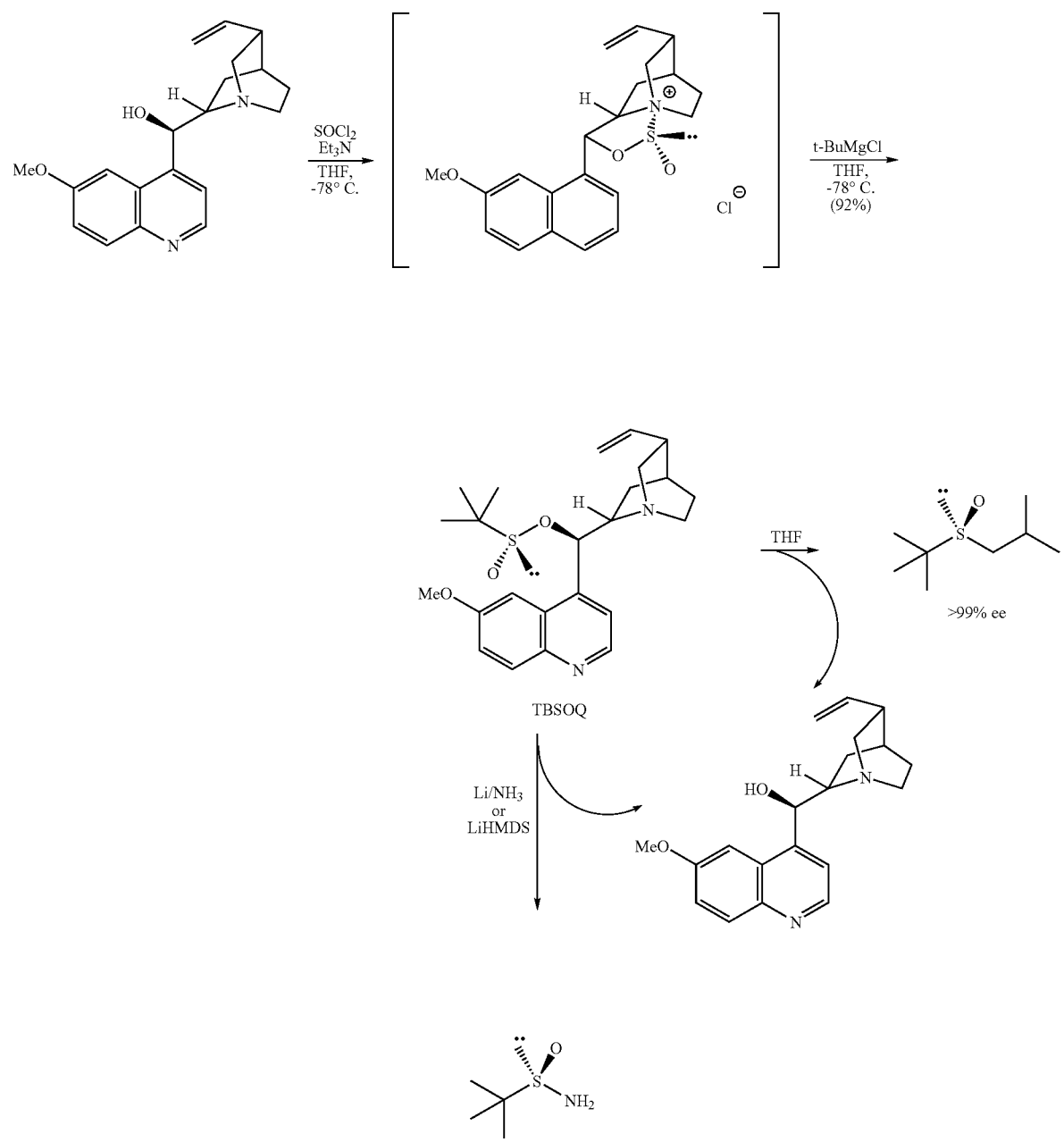

TABLE 1

Preparation of TBSOQ

| Entry | Ligand | R₁M | Solvent | Temp (°C) | Product | Yield (%) | d.e. (%) |
|---|---|---|---|---|---|---|---|
| 1 | (−)-Quinine | t-BuMgCl | THF | −78 | (R)- | 92 | >99 |
| 2 | [structure: HO-CH(Ph)-CH(CH₃)-N-pyrrolidine] | t-BuMgCl | THF | −78 | | | 15 |

TABLE

Nucleophilic dispacement of TBSOQ to form sulfoxide or sulfinylamine

| Entry | Base | R₁M | R₂M | Product | Yield (%) | E.e. (%) |
|---|---|---|---|---|---|---|
| | Et₃N | t-BuMgCl | PhMgCl | t-Bu-S(O)-Ph | 93 | >99 |
| | Et₃N | t-BuMgCl | ⁱPrMgCl | t-Bu-S(O)-iPr | 91 | >99 |
| | Et₃N | t-BuMgCl | sec-BuMgCl | t-Bu-S(O)-CH₂CH(CH₃)₂ | 95 | >99 |
| | Et₃N | t-BuMgCl | CH₂=C(OLi)(OtBu) | t-Bu-S(O)-CH₂-C(O)-O-tBu | 81 | >99 |
| | Et₃N | p-Tolyl₂Cu p-TolylAlEt₂ | MeMgCl | p-Tolyl-S(O)-Me | 88 | >99 |
| | Et₃N | t-BuMgCl | LiHMDS | t-Bu-S(O)-NH₂ | 70 | 96 |

Scheme 16

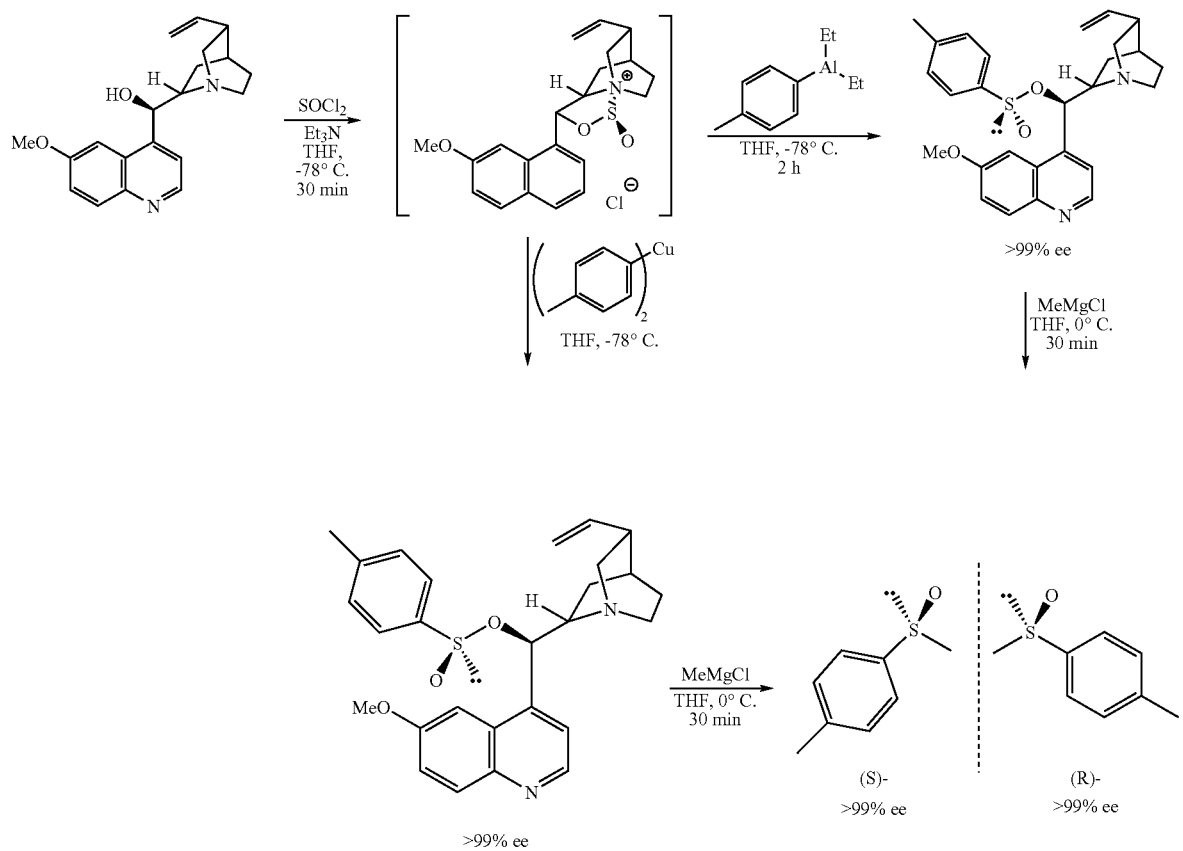

Novel Practical Process for Preparation of Enantiopure Sulfinylamines

Supporting Information

General. Unless otherwise noted, all reagents were obtained from commercial suppliers and were used without further purification. All anhydrous solvents were used for the reaction, and were purchased from Aldrich. All reactions, unless otherwise noted, were carried out in oven dried glassware under inert argon atmosphere. Chromatography was carried out using Silicycle 60, 230–400 mesh silica gel. Thin-layer chromatography (TLC) analysis was performed with Merk Kieselgel 60 F 254 plates, and was visualized using UV light and/or phosphomolybdic staining. $^1$H NMR and proton-decoupled $^{13}$C NMR spectra were obtained with a Varian Inova 300 spectrometer in CDCl$_3$ with TMS as an internal standard at room temperature. Proton and carbon spectra chemical shifts were reported using TMS and/or CDCl$_3$ as an internal standard at 0 ppm and at 77.23 ppm, respectively. Diastereomeric ratios were determined on $^1$H NMR spectrum analyses. Elemental analyses were performed by Quantitative Technologies, Inc., Whitehouse, N.J. Enantiomeric excesses were obtained by chiral HPLC analysis using Chiralpak A S, Chiralcel O B, or Chiralcel O D column.

Preparation of TBSOQ:

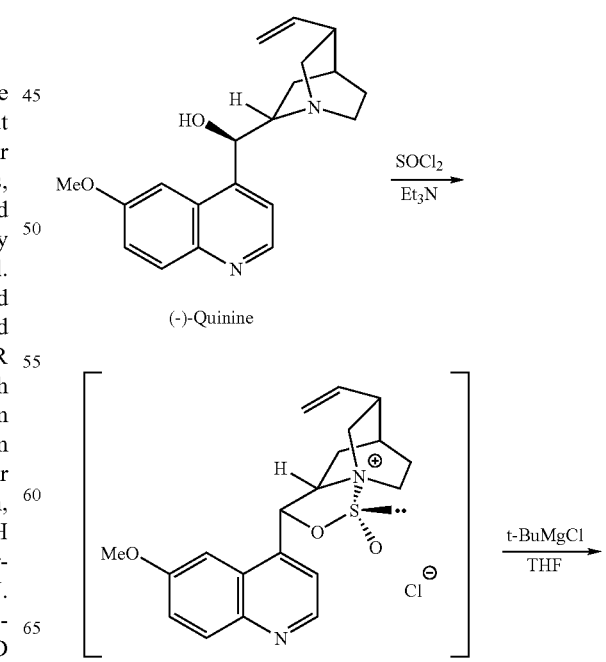

-continued

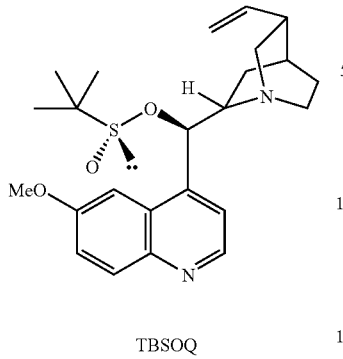

TBSOQ

A 4-neck 1 L round-bottom flask fitted with a mechanical stirrer, addition funnel, temperature probe, and argon inlet was charged with (−)-quinine (3.0 g, 9.25 mmol, 1.0 equiv.) and THF (80 mL). The solution was chilled to −60° C., thionyl chloride (0.75 mL, 10.28 mmol, 1.1 equiv.) was added dropwise via a syringe. The mixture was stirred for 10 min, followed by addition of Et$_3$N (2.9 mL, 20.85 mmol, 2.2 equiv.) over a 5 min period. The resultant mixture was stirred at between −37~−45° C. for 1 hr, followed by addition of tert-butyl magnesium chloride (19 mL, 1.0 M in THF, 19.0 mmol, 2.05 equiv.) at −78° C. The resultant clear reaction was stirred at −75° C. for 2 h and monitored by TLC analysis. Once the reaction was completed, the reaction was quenched with saturated NaHCO$_3$ aqueous solution (90 mL), and the mixture was diluted with ethyl acetate (150 mL) and warmed to ambient temperature with stirring. The phases were allowed to separate and the aqueous phase was removed. The aqueous phase was extracted with ethyl acetate (100 mL). The combined organic phases were washed with brine (60 mL), dried, and evaporated to give diastereopure TBSOQ. The yellowish oily product was purified by flash column chromatography (eluent with 5% MeOH in AcOEt) to remove impurities derived from the starting material, and give pure TBSOQ as colorless oil which turned into white solid after standing at ambient temperature (3.6 g, 91% yield). The diastereomeric excess is >99% as determined by $^1$H NMR spectrum and HPLC.

$^1$H NMR (CDCl$_3$) δ

$^{13}$C NMR (CDCl$_3$) δ

HPLC method: Symmetry C-18, 4.6 mm×150 mm, 5 μ; 222 nm; 0.5 mL/min.; MeOH/H$_2$O 80:20.

(S)-tert-Butyl phenylsulfoxide

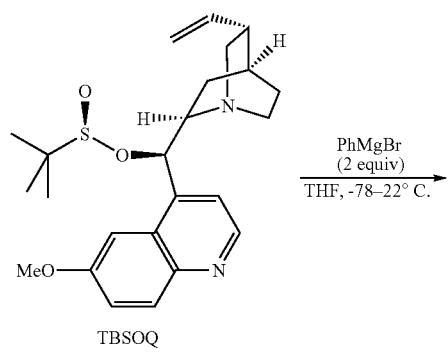

TBSOQ

PhMgBr
(2 equiv)
————————→
THF, −78–22° C.

-continued

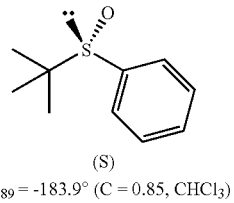

(S)

[ ]$_{589}$ = −183.9° (C = 0.85, CHCl$_3$)

A solution of TBSOQ (1.79 g, 4.14 mmol, 1.0 equiv.) in THF (20 mL) at −78° C. under argon was charged dropwise with phenylmagnesium bromide (2.8 mL, 3.0 M in Et$_2$O, 8.3 mmol, 2.0 equiv.). After being stirred at −78° C. for 1 h, the reaction mixture was warmed to 22° C., and the reaction was monitored by TLC analysis. The reaction was quenched by 20% NaCl (15 mL) aqueous solution and diluted with EtOAc (30 mL). After phase separation, the organic phase was extracted once with EtOAc. The combined organic phases was washed with 20% NaCl (10 mL) aqueous solution, dried over Na$_2$SO$_4$, and concentrated to give the mixture of (S)-tert-Butyl phenylsulfoxide and (−)-quinine, which was purified by flash chromatography eluted with EtOAc to afford (S)-t-butyl isobutyllsulfoxide (0.76 g, 93%) in >99% ee. The enantiomeric purity was analyzed by chiral HPLC analysis. The configuration at sulfur atom was deduced by comparison of the optical rotation with that of reported in literature.

$^1$H NMR (300 MHz, CDCl$_3$): δ 1.20 (s, 9H), 7.53 (m, 3H), 7.63 (m, 3H). $^{13}$C NMR (75 MHz, CDCl$_3$): δ23.0, 56.0, 126.6, 128.6, 131.4, 140.2. [α]$^{22}_D$=−184 (c, 0.84, CHCl$_3$); Lit.$^2$+175.

(R)-tert-Butyl (tert-butylsulfinyl)acetate
(R$_2$=LiCH$_2$COOBu-t)

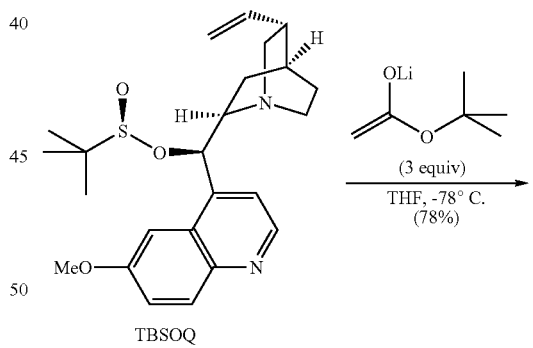

TBSOQ

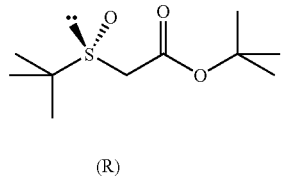

(R)

A solution of diisopropylamine (0.3 mL, 2.14 mmol) in THF (4 mL) at −15° C. was added n-BuLi (1.3 mL, 1.6 M in hexane, 2.08 mmol) slowly. The mixture was warmed to 0° C., stirred for 30 min and cooled to −45° C., followed by addition of tert-butyl acetate (0.28 mL 2.08 mmol, 1.0 eq). The reaction mixture was stirred for 30min and was cooled to −78° C. A solution of TBSOQ (300 mg, 0.70 mmol) in THF (2 mL) was added slowly while keeping the reaction mixture at −78° C.~−75° C. and the reaction was monitored by TLC analysis. The reaction was worked up and the crude product was purified by flash chromatography eluted with EtOAc-MeOH (5:1) to afforded the title compound (133 mg) in a 81% yield and >99% ee. $^1$H NMR (CDCl$_3$): δ 1.28 (s, 9H), 1.51 (s, 9H), 3.29 (d, 1H), 3.47 (d, 1H). $^{13}$C NMR (CDCl$_3$): δ 22.7, 27.9,52.8, 54.0, 83.1, 1654.

Chiral BPLC method: Chiralpak AS 4.6 mm×250 mm, 10 μ; 222 nm; 0.8 mL/min.; Hex/EtOH 90:10; (S)-isomer, $t_R$=11.2 min; (R)-isomer $t_R$=13.2 min. (99.8% ee).

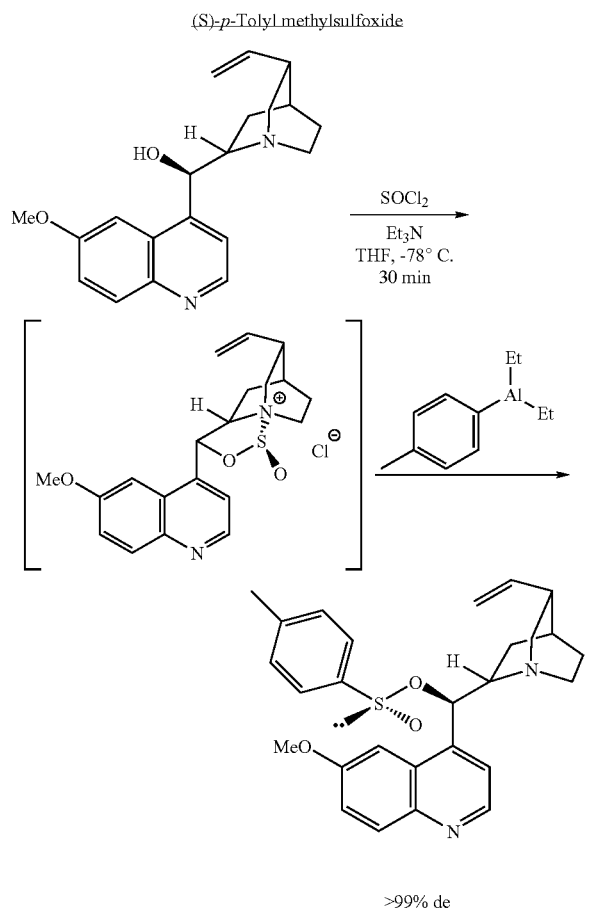

p-Tolylmagnesium bromide (15 mL, 1.0 M in THF, 15 mmol, 2.1 equiv.) was added to a solution of diethylaluminium chloride (8.3 mL, 1.8 M in toluene, 15 mmol, 2.1 equiv.) at −60° C. to −50° C. The mixture was then cooled to −78° C. and stirred for 0.5 hr. In another 3-neck 250 mL round-bottom flask fitted with addition funnel, temperature probe, and argon inlet was charged with (−)-quinine (2.27 g, 7.0 mmol, 1.0 equiv.) and TBF (48 mL). The solution was chilled to −75° C., thionyl chloride (0.54 mL, 7.40 mmol, 1.05 equiv.) was added dropwise via a syringe. The mixture was stirred for 10 min, followed by addition of Et$_3$N (2.14 mL, 15.4 mmol, 2.2 equiv.) over a 5 min period. The resultant mixture was stirred for 30 min, followed by addition of the above-mentioned p-tolyl diethylaluminium at the same temperature. The resultant clear reaction was stirred at −75° C. for 2 h and monitored by TLC analysis. The reaction was then quenched with saturated aqueous solution of Rochelle's salt and extracted with ethyl acetate (2×25 mL). The organic extracts were washed with brine and evaporated. The residue was purified by flash chromatography eluted with 5% methanol in EtOAc to afford p-tolylquininyl sulfoxide ester (2.5 g) in 78% yield.

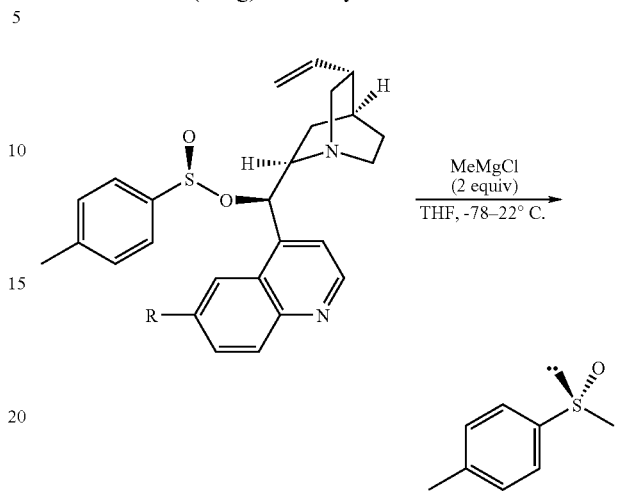

Methyl magnesium chloride (100 uL, 3.0 M in THF, 0.3 mmol, 1.4 equiv) was added to a solution of the p-tolylquininyl sulfoxide ester (100 mg, 0.216 mmol) in TBF (2 mL) at −60° C. to −78° C. The reaction mixture was then stirred at −78° C. for 30 min and the reaction was monitored by TLC analysis. The reaction was then quenched with saturated KHCO$_3$ aqueous solution and extracted with ethyl acetate (2×10 mL). The organic extracts were washed with brine and evaporated. The residue was purified by flash chromatography eluted with EtOAc to afford the title compound (30 mg) in 88% yield. The diastereomeric excess is >99% as determined by HPLC. The absolute configuration is deduced from comparison with authentic sample.

Chiral HPLC method: Chiralpak AS, 90:10 Hex/EtOH, 1 min/mL

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

The invention claimed is:

1. A method of preparing an amine stereoisomer, which comprises stereoselectively reducing a sulfinylimine that bears on the sulfinyl group a residue of an alcohol, thiol or amine, or reacting a sulfinylimine stereoisomer that bears on the sulfinyl group a residue of an alcohol, thiol or amine with a source of a nucleophile, to afford a sulfinylimine stereoisomer, followed by contacting the sulfinylamine stereoisomer with a reagent suitable for the cleavage of a sulfur-nitrogen bond, to afford an amine stereoisomer.

2. A method as claimed in claim 1, wherein the sulfinylimine is a sulfinylimine stereoisomer.

3. A method as claimed in claim 1, wherein the residue of the alcohol, thiol or amine is in stereoisomeric form.

4. A method as claimed in claim 1, wherein the residue of the alcohol, thiol or amine is a residue of an optionally N-substituted beta-amino alcohol, thiol or amine.

5. A method as claimed in claim 4, wherein the optionally N-substituted beta-amino alcohol, thiol or amine is a compound of the general formula

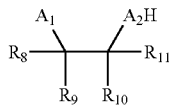

wherein $A_1$ is $R_7N$ or $(R_{7'})R_{7''}N$, $R_7$ represents hydrogen or -L-$R_{7a}$ in which -L- represents a bond, —CO—, —(CO)O—, —(CO)NR$_{7b}$—, —SO—, —SO$_2$—, or —(SO$_2$)O—, each of $R_{7a}$ and $R_{7b}$ independently represents substituted or unsubstituted alkyl, substituted or unsubstituted aralkyl, substituted or unsubstituted heteroalkyl, substituted or unsubstituted aryl or substituted or unsubstituted heteroaryl, and $R_{7'}$ and $R_{7''}$ are as defined for $R_{7a}$, or $R_{7'}$ and $R_{7''}$ together with the nitrogen atom to which they are attached and, optionally $R_8$, form an unsubstituted or substituted heterocyclic group, or $R_{7'}$ together with the nitrogen atom to which it is attached and the carbon atom to which the nitrogen atom is attached forms an unsubstituted or substituted heterocyclic group; $A_2$ is O, S or NR$_{7c}$ in which R$_{7c}$ is substituted or unsubstituted alkyl, substituted or unsubstituted aralkyl, substituted or unsubstituted heteroalkyl, substituted or unsubstituted aryl or substituted or unsubstituted heteroaryl; and each of $R_8$, $R_9$, $R_{10}$ and $R_{11}$ is independently hydrogen, substituted or unsubstituted alkyl, substituted or unsubstituted aralkyl, substituted or unsubstituted heteroalkyl, substituted or unsubstituted aryl or substituted or unsubstituted heteroaryl, or $R_8$ and $R_{11}$ together form a substituted or unsubstituted alkylene or heteroalkylene chain.

6. A method as claimed in claim 5, wherein $A_2$ is O.

7. A method as claimed in claim 5, wherein each of $R_8$ $R_9$, $R_{10}$ and $R_{11}$ is independently selected from hydrogen, (1–4C)alkyl and phenyl, or the alcohol is selected from (N-methylpyrrolidin-2-yl) diphenylmethanol, quinine, quinine, hydroquinine, cinchonidine, cinchonine, hydrocinchonidine and ethyl hydrocupreine.

8. A method as claimed in claim 7, wherein $A_1$ is $R_7N$ wherein $R_7$ represents —SO$_2$—$R_{7a}$ in which $R_{7a}$ represents (1–6C)alkyl, (6–10C)aryl(1–4)alkyl or (6–10C)aryl in which any aryl group is unsubstituted or substituted by one, two or three substituents selected independently from halogen, (1–4C) alkyl and (1–4C)alkoxy, or $A_{1'}$ is $(R_{7'})R_{7''}N$ wherein $R_{7'}$ and $R_{7''}$ each independently represents a (1–4C) alkyl group or together with the nitrogen to which they are attached represent a pyrrolidine group that may bear one or two methyl substituents, or the alcohol is selected from (N-methylpyrrolidin-2-yl) diphenylmethanol, quinine, quinidine, hydroquinine, cinchonidine, cinchonine, hydrocinchonidine and ethyl hydrocupreine.

9. A method as claimed in claim 7, wherein $A_{1'}$ is $R_7N$ and the residue of the alcohol, thiol or amine is a residue of an optionally N-substituted 2-amino-1-phenylpropanol, 2-amino-2-methyl-1-phenylpropanol, 1-amino), -phenyl-2-propanol, 1-amino-1-phenyl-2-methyl-2-propanol, 1-amino-1-phenyl-2-ethyl-2-butanol, 1-amino-2-indanol, 2-aminoindan-1-ol, 1-amino-2-hydroxy 1,2,3,4-tetrahydronaphthalene or 2-amino-1-hydroxy-1,2,3,4-tetrahydronaphthalene, or $A_{1'}$ is $(R_{7'})R_{7''}N$ and the alcohol is selected from 2-N,N-dimethylamino-1-phenyl-2-propanol, 2-N,N-dibutylamino-1-phenylpropanol, 2-pyrrolidin-1-yl-1-phenylpropanol, 2-(2-methylpyrrolidin-1-yl)-1-phenylpropanol, 2-(2,5-dimethylpyrrolidin-1-yl)-1-phenylpropanol, 2-N,N-dimethylamino2-methyl-1phenylpropanol, (N-methylpyrrolidin-2-yl) diphenylmethanol, 1-pyrrolidin-1-ylindan-2-ol, 3-benzyloxy-2-N,N-dimethylamino-1-phenylpropan-2ol, quinine, quinidine, hydroquinine, cinchonidine, cinchonine, hydrocinchonidine and ethyl hydrocupreine.

10. A method as claimed in claim 4, wherein the sulfinylimine has been prepared by contacting an iminometal with a 1,2,3-oxathiazolidine-S-oxide, a 1,2,3-dithiazolidine-S-oxide or a 1,2,3-azathiazolidine-S-oxide.

11. A method as claimed claim 10, wherein the 1,2,3-oxathiazolidine-S-oxide, 1,2,3-dithiazolidine-S-oxide or 1,2,3-azathiazolidine-S-oxide is a compound of formula 3 or 3'

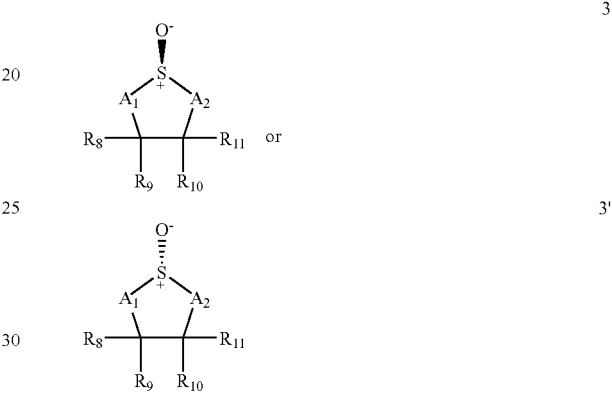

wherein $A_1$ is $R_7N$ or $(R_{7'})R_{7''}N^+Q^-$ in which Q– is an anion, $R_7$ represents hydrogen or -L-$R_{7a}$ in which -L- represents a bond, —CO—, —(CO)O—, —(CO)NR$_{7b}$—, —SO—, —SO$_2$—, or —(SO$_2$)O—, each of $R_{7a}$ and $R_{7b}$ independently represents substituted or unsubstituted alkyl, substituted or unsubstituted aralkyl, substituted or unsubstituted heteroalkyl, substituted or unsubstituted aryl or substituted or unsubstituted heteroaryl, and $R_{7'}$ and $R_{7''}$ are as defined for $R_{7a}$, or $R_{7'}$ and $R_{7''}$ together with the nitrogen atom to which they are attached and, optionally $R_8$, form an unsubstituted or substituted heterocyclic group, or $R_{7'}$ together with the nitrogen atom to which it is attached and the carbon atom to which the nitrogen atom is attached forms an unsubstituted or substituted heterocyclic group; $A_2$ is O, S or NR$_{7c}$ in which R$_{7c}$ is substituted or unsubstituted alkyl, substituted or unsubstituted aralkyl, substituted or unsubstituted heteroalkyl, substituted or unsubstituted aryl or substituted or unsubstituted heteroaryl; and each of $R_8$, $R_9$, $R_{10}$ and $R_{11}$ is independently hydrogen, substituted or unsubstituted alkyl, substituted or unsubstituted aralkyl, substituted or unsubstituted heteroalkyl, substituted or unsubstituted aryl or substituted or unsubstituted heteroaryl, or $R_8$ and $R_{11}$ together form a substituted or unsubstituted alkylene or heteroalkylene chain;

the iminometal is a compound of formula 1'

wherein N is CdZ, BaZ, Na, K, MgZ, ZnZ, Li, MnZ, CuZ, TiZ$_3$ or In and Z is an anion.

12. A method as claimed in claim 11, wherein the 1,2,3-oxathiazolidine-S-oxide, 1,2,3-dithiazolidine-S-oxide or 1,2,3-azathiazolidine-S-oxide is a stereoisomer of formula 5

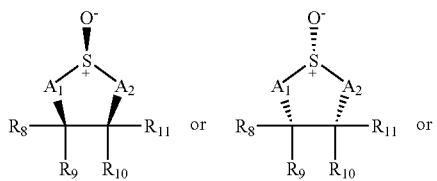

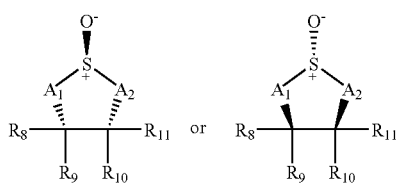

13. A method as claimed in claim 11, wherein the amine stereoisomer is a compound of formula 5 or 5'

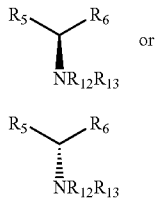

or a pharmaceutically acceptable salt, solvate, clathrate, hydrate or prodrug thereof, wherein R$_5$ and R$_6$ are independently substituted or unsubstituted alkyl, substituted or unsubstituted heteroalkyl, substituted or unsubstituted aralkyl, substituted or unsubstituted aryl or substituted or unsubstituted heteroaryl, or R$_5$ and R$_6$ together with the carbon atom to which they are attached form a substituted or unsubstituted cycloalkyl group, and R$_{12}$ and R$_{13}$ together with the nitrogen atom to which they are attached form a heterocycle, or each of R$_{12}$ and R$_{13}$ is independently hydrogen, substituted or unsubstituted alkyl, substituted or unsubstituted aralkyl, or substituted or unsubstituted aryl; and the sulfinylimine stereoisomer is a compound of formula 4 or 4'

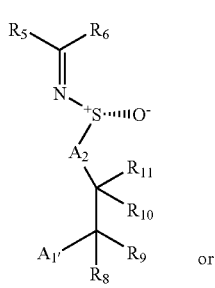

-continued

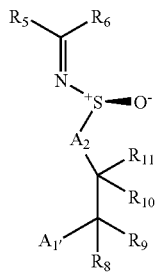

wherein A$_{1'}$ represents R$_7$N or (R$_{7'}$)R$_{7''}$N.

14. A method as claimed in claim 13, wherein A$_2$ is O.

15. A method as claimed in claim 14, wherein R$_5$ and R$_6$ are independently substituted or unsubstituted alkyl, substituted or unsubstituted heteroalkyl, substituted or unsubstituted aralkyl, substituted or unsubstituted aryl or substituted or unsubstituted heteroaryl; the 1,2,3-oxathiazolidine-S-Oxide is a c pound of the formula 3 or 3'

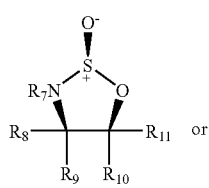

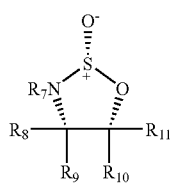

in which R$_7$ represents hydrogen or -L-R$_{7a}$ in which L is a bond or SO$_2$ and R$_{7a}$ is substituted or unsubstituted alkyl, substituted or unsubstituted a aralkyl, substituted or unsubstituted heteroalkyl, substituted or unsubstituted aryl or substituted or unsubstituted heteroaryl; Z in the iminometal of formula 1' is Cl, Br or I; and the sulfinylimine stereoisomer is a compound of formula

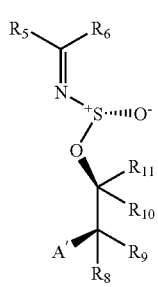

-continued

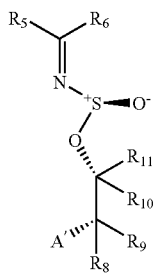
4'

16. A method as claimed in claim 13, wherein $R_{12}$ and $R_{13}$ are both hydrogen.

17. A method as claimed in claim 10, wherein the 1,2,3-oxathiazolidine-S-oxide, 1,2,3-dithiazolidine-S-oxide or 1,2,3-azathiazolidine-S-oxide has been prepared by reacting an optionally N-substituted beta-amino alcohol, thiol or amine with a thionyl halide.

18. A method as claimed in claim 1, which further comprises the step of alkylating the amine stereoisomer.

19. A method as claimed in claim 1, wherein the amine stereoisomer is a compound of formula

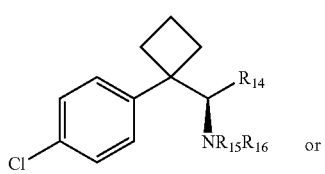
7 or

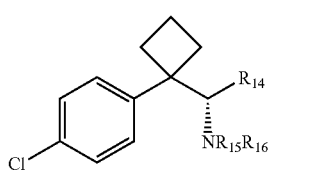
7' or a pharmaceutically acceptable salt, solvate, clathrate, hydrate or prodrug thereof, wherein $R_{14}$ is substituted or unsubstituted alkyl, substituted or unsubstituted heteroalkyl, substituted or unsubstituted aralkyl or substituted or unsubstituted aryl, and $R_{15}$ and $H_{16}$ together with the nitrogen to which they are attached form a heterocycle, or each of $H_{15}$ and $R_{16}$ is independently hydrogen, substituted or unsubstituted alkyl, substituted or unsubstituted heteroalkyl, substituted or unsubstituted aralkyl or substituted or unsubstituted aryl.

20. A method as claimed in claim 19, in which the amine stereoisomer is a compound of formula

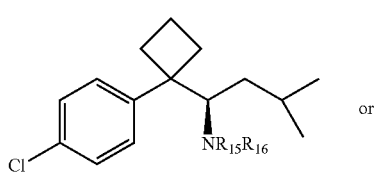
14

-continued

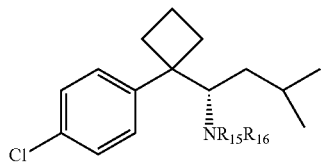
14'

21. A method as claimed in claim 19, wherein $R_{15}$ and $R_{16}$ are both hydrogen.

22. A method as claimed in claim 10 wherein the amine stereoisomer is a compound of formula

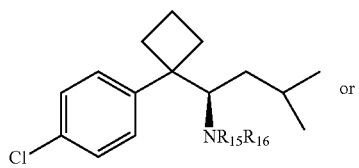
14 or

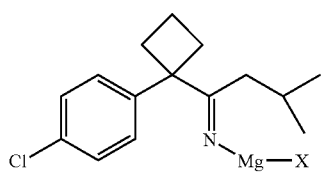
14' wherein $R_{15}$ and $R_{16}$ are both hydrogen and the metal imine is a compound of formula

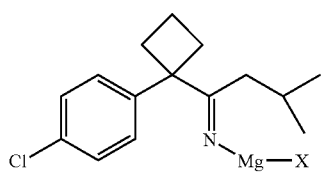

that has been obtained by contacting a compound of formula

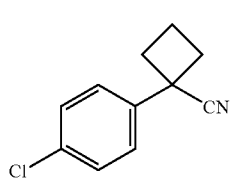
15 with a compound of formula i-BuMg-X wherein X is a halogen.

23. A method as claimed in claim 10, wherein the 1,2,3-oxathiazolidine-S-oxide is a compound of the formula

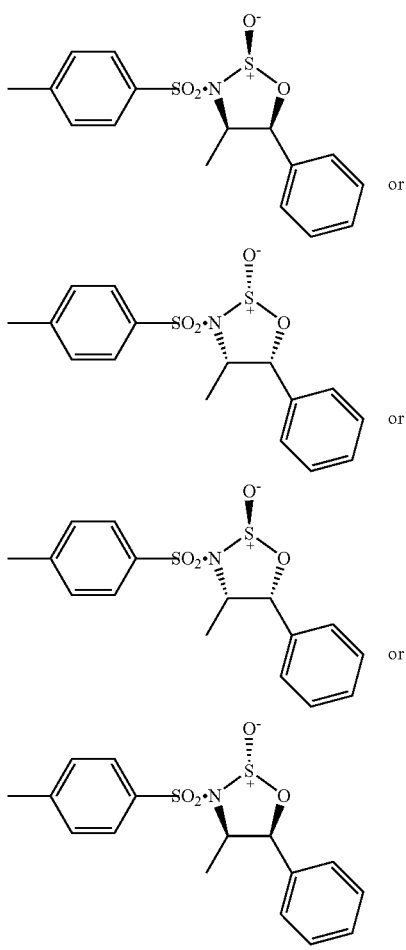

24. A method as claimed in claim 1, wherein the sulfinylimine is reduced using a hydride reducing agent.

25. A method as claimed in claim 24, wherein the hydride reducing agent is NaBH$_4$.

26. A method as claimed in claim 1, in which the reagent suitable for the cleavage of a sulfur-nitrogen bond is an acid.

27. A method as claimed in claim 26 wherein the acid is HCl.

28. A method as claimed in claim 1, in which reaction of the sulfinylamine stereoisomer with the reagent suitable for the cleavage of a sulfur-nitrogen bond also affords an optionally N-substituted beta-aminoalcohol, and this optionally N-substituted beta-aminoalcohol is recovered, converted into 1,2,3-oxathiazolidine-S-oxide and recycled.

29. A method as claimed in claim 1, wherein the stereoselective reduction of the sulfinylimine is performed using a stereoselective reducing agent.

30. A method as claimed in claim 1, in which the amine stereoisomer is selected from Alacepril, Benazepril, Benazeprilate, Ceronapril, Cilazapril, Cilazaprilat, Delapril, Enalapril, Enalaprilat, Fasidotril, Fosinopril, Imidapril, Imidaprilat, Libenzapril, Lisinopril, Moexipril, Moexiprilat, Moveltipril, Pentopril, Perindopril, Quinapril, Quinaprilat, Ramipril, Sampatrilat, Spirapril, Spiraprilat, Temocapril, Temocaprilate, Trandolapril, Trandolaprilate, Utibapril, Utibaprilat, Zabicipril, Zabiciprilat, Bucillamine, Penicillamine, Thiamphenicol, Cefprozil, Cephalexin, Cephaloglycin, Cilastatin, Alafosfalin, Ethambutol, Sertraline, Tametraline, Acetylcysteine, Selegiline, Azaserine, Dorzolamide, Colchicine, Dilevalol, Enalapril, Methyldopa, Metaraminol, Acivicin, Melphalan, Ubenimex, Tmsulosin, Tirofiban, Dilevalol, N-dodecyl-N-methylephedrinium, Ofenucine, Tinofedrine, Aceglutamide, 1-ephedrine, levopropylhexedrine, (+)- and (−)-Norephedrine, Phenylpropanolamine, Pseudoephedrine, d-farm, (R)- and (S)-Tamsulosin, Dimepheptanol, Lofentanil, Tilidine hydrochloride (+)-trans, Ciramadol, Enadoline, Lefetamine, Spiradoline, (+)-Etoxadrol, Levoxadrol, (R)-Amphetamine, Clobenzorex, Dexfenfluramine, Dextroamphetamine, Etilamfetamine, Fenfluramine, Levofenfluramine, Phenylpropanolamine, Cetirizine, (R)- and (S)-Baclofen, (R)- and (S)-Sibutramine, and pharmaceutically acceptable salts thereof.

31. A method as claimed in claim 1, wherein the sulfinylimine stereoisomer is reacted with a source of a nucleophile selected from a nitrile, a Grignard reagent and an organolithium.

32. A method as claimed in claim 31, wherein the sulfinylimine stereoisomer is reacted with a nitrile, and the resultant amine stereoisomer bearing a nitrile group is hydrolyze to afford an amino acid.

* * * * *